United States Patent
Klee et al.

(10) Patent No.: US 10,899,861 B2
(45) Date of Patent: Jan. 26, 2021

(54) POLYMERIZABLE POLYACIDIC POLYMER

(71) Applicant: DENTSPLY SIRONA inc., York, PA (US)

(72) Inventors: Joachim Klee, Radolfzell (DE); Caroline Renn, Singen (DE); Florian Szillat, Constance (DE); Oliver Elsner, Radolfzell (DE); Christian Scheufler, Engen (DE); Ulrich Lampe, Dusseldorf (DE); Helmut Ritter, Wuppertal (DE)

(73) Assignee: DENTSPLY SIRONA INC., York, PA (US)

( * ) Notice: Subject to any disclaimer, the term of this patent is extended or adjusted under 35 U.S.C. 154(b) by 31 days.

(21) Appl. No.: 15/754,303

(22) PCT Filed: Sep. 9, 2016

(86) PCT No.: PCT/EP2016/071304
§ 371 (c)(1),
(2) Date: Feb. 22, 2018

(87) PCT Pub. No.: WO2017/042333
PCT Pub. Date: Mar. 16, 2017

(65) Prior Publication Data
US 2018/0237567 A1 Aug. 23, 2018

(30) Foreign Application Priority Data
Sep. 9, 2015 (EP) .................................... 15184510

(51) Int. Cl.
| | | |
|---|---|---|
| *A61F 2/00* | (2006.01) | |
| *C08F 220/56* | (2006.01) | |
| *C08F 8/30* | (2006.01) | |
| *C08F 290/12* | (2006.01) | |
| *C08F 220/06* | (2006.01) | |
| *C07C 233/20* | (2006.01) | |

(52) U.S. Cl.
CPC .......... *C08F 220/56* (2013.01); *C07C 233/20* (2013.01); *C08F 8/30* (2013.01); *C08F 220/06* (2013.01); *C08F 290/126* (2013.01); *C08F 2800/10* (2013.01); *C08F 2800/20* (2013.01); *C08F 2810/30* (2013.01); *C08F 2810/50* (2013.01)

(58) Field of Classification Search
CPC combination set(s) only.
See application file for complete search history.

(56) References Cited

U.S. PATENT DOCUMENTS

| | | |
|---|---|---|
| 3,655,605 A | 4/1972 | Smith |
| 3,814,717 A | 6/1974 | Wilson |
| 4,089,830 A | 5/1978 | Tezuka |
| 4,143,018 A | 3/1979 | Crisp |
| 4,209,434 A | 6/1980 | Crisp |
| 4,298,738 A | 11/1981 | Lechtken |
| 4,317,681 A | 3/1982 | Beede |
| 4,324,744 A | 4/1982 | Lechtken |
| 4,360,605 A | 11/1982 | Schmitt |
| 4,374,936 A | 2/1983 | Tomoika |
| 4,376,835 A | 3/1983 | Scmitt |
| 4,385,109 A | 5/1983 | Lechtken |
| 5,154,762 A | 10/1992 | Mitra |
| 5,501,727 A | 3/1996 | Wang |
| 5,545,676 A | 8/1996 | Palazzotto |
| 2003/0069327 A1* | 4/2003 | Walz ................... A61K 6/0038 523/116 |

FOREIGN PATENT DOCUMENTS

| | | |
|---|---|---|
| EP | 0173567 A2 | 3/1986 |
| EP | 2329807 A1 | 6/2011 |
| EP | 2705827 A1 | 3/2014 |
| WO | 03011232 A1 | 2/2003 |
| WO | 2012084206 A1 | 6/2012 |
| WO | WO2012/084206 * | 6/2012 |
| WO | 2014040729 A1 | 3/2014 |

OTHER PUBLICATIONS

International Search Report dated Sep. 22, 2016.

* cited by examiner

*Primary Examiner* — Monique R Peets
(74) *Attorney, Agent, or Firm* — Dentsply Sirona Inc.

(57) ABSTRACT

The present invention relates to a polymerizable polyacidic polymer and to a process for preparing the polymerizable polyacidic polymer. Furthermore, the present invention relates to an aqueous dental composition comprising the polymerizable polyacidic polymer, to a use of the polymerizable polyacidic polymer for the preparation of a dental composition and to an acrylic acid derivative copolymer.

11 Claims, No Drawings

POLYMERIZABLE POLYACIDIC POLYMER

FIELD OF THE INVENTION

The present invention relates to a polymerizable polyacidic polymer. The present invention also relates to a process for preparing the polymerizable polyacidic polymer. Furthermore, the present invention relates to an aqueous dental composition comprising the polymerizable polyacidic polymer. Furthermore, the present invention relates to a use of the polymerizable polyacidic polymer of the present invention for the preparation of a dental composition. Finally, the present invention relates to a copolymer of a specific acrylic acid derivative.

An aqueous dental composition comprising the polymerizable polyacidic polymer according to the invention provides an acid-resistant cured dental composition having excellent mechanical properties and long-term mechanical and chemical resistance.

BACKGROUND OF THE INVENTION

Dental restorative materials are used for restoring the function, morphology and integrity of dental structures damaged by physical damage or caries-related decay of enamel and/or dentin. Dental restorative materials are required to have high biocompatibility, good mechanical properties and mechanical and chemical resistance over a long period of time given the harsh conditions for a restorative material in the buccal cavity.

Dental restorative materials include aqueous dental compositions such as glass ionomer cements having good biocompatibility and good adhesion to the dental hard tissues. Moreover, aqueous dental compositions such as glass ionomer cements may provide cariostatic properties through the release of fluoride ions. Glass ionomer cements are cured by an acid-base reaction between a reactive glass powder and a polyalkenoic acid. However, conventional glass ionomer cements have a relatively low flexural strength and are brittle due to salt-like structures between the polyacid and the basic glass.

The mechanical properties of aqueous dental compositions such as glass ionomer cements may be improved by the selection of the polyacidic polymer. For example, a polymer having polymerizable moieties as pendant groups can be crosslinked in order to increase the mechanical resistance of the resulting glass ionomer cement.

Japanese Patent Publication No. 2005-65902A discloses a dental adhesive composition comprising, as a polymerizable monomer containing a particular carboxylic acid, a carboxylic acid compound having a (meth)acryloyl group and a carboxyl group which are bound to an aromatic group. However, such a polymerizable monomer having an ester group quickly degrades in an acidic medium.

Chen et al. and Nesterova et al. (Chen et al., J. Appl. Polym. Sci., 109 (2008) 2802-2807; Nesterova et al., Russian Journal of Applied Chemistry, 82 (2009) 618-621) disclose copolymers of N-vinylformamide with acrylic acid and/or methacrylic acid, respectively. However, none of these documents mentions the introduction of a further polymerizable moiety into the copolymer.

WO2003/011232 discloses water-based medical and dental glass ionomer cements that can be post-polymerized after the cement reaction. The dental glass ionomer cements consist of two separate polymers, wherein one of the polymers has a pendant post-polymerizable moiety linked to the polymer through an ester bond. However, this ester bond between the polymer and the polymerizable moieties is again prone to hydrolytic cleavage in acidic media. Moreover, crosslinking of the glass ionomer may lead to the shrinkage of the dental composition in particular when the molecular weight of the crosslinking polymer is low.

WO2012/084206 A1 discloses a process for producing a water-soluble, hydrolysis-stable, polymerizablepolymer, comprising a) a step of copolymerizing a mixture comprising
   (i) a first copolymerizable monomer comprising at least one optionally protected carboxylic acid group and a first polymerizable organic moiety, and
   (ii) a second copolymerizable monomer comprising one or more optionally protected primary and/or secondary amino groups and a second polymerizable organic moiety,
   for obtaining an amino group containing copolymer;
b) a step of coupling to the amino group containing copolymer a compound having a polymerizable moiety and a functional group reactive with an amino group of repeating units derived from the second copolymerizable monomer in the amino group containing copolymer obtained in the first step wherein the optionally protected amino group is deprotected, so that polymerizable pendant groups are linked to the backbone by hydrolysis-stable linking groups, and, optionally, a step of
deprotecting the protected carboxylic acid group after step (a) or step (b), for obtaining a polymerizable polymer.

US 2003/0069327 A1 discloses a dental composition comprising bisacrylamides, which upon polymerization result in crosslinked, water-insoluble polymers.

SUMMARY OF THE INVENTION

It is an object of the present invention to provide a polymerizable polyacidic polymer representing a valuable and versatile component for the preparation of an aqueous dental composition, preferably for the preparation of a dental glass ionomer composition, whereby such aqueous dental composition provides improved mechanical properties including high flexural strength and a clinically relevant adhesion to tooth structure after curing, as well as hydrolysis-stability in an aqueous medium before and after curing, in particular in an acidic medium.

The present invention provides a polymerizable polyacidic polymer having repeating units of the following formula (I):

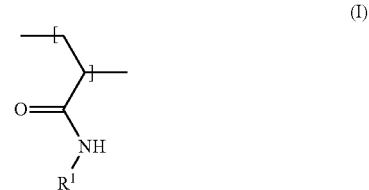

wherein $R^1$ represents a group of the following formula (II):

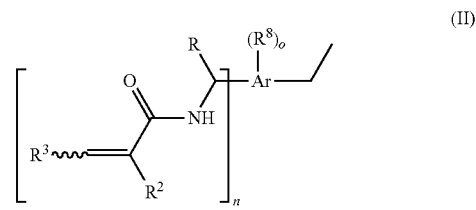

wherein
Ar is an aromatic group which may be further substituted,
$R^2$ and $R^3$,
  which may be the same or different, independently represent a hydrogen atom, or a $C_{1-6}$ alkyl group which may be substituted with a carboxylic acid group;
R which may be the same or different when more than one R is present, represents a hydrogen atom, a carboxylic acid group, a $COOR^a$ group, a $CONHR^b$ group, or a $CONR^c_2$ group, wherein $R^a$, $R^b$, and $R^c$ represent a $C_{1-6}$ alkyl group;
$R^8$ represents a halogen atom or a group selected from —OH, —$OR^d$, —$NR^eH$, —$NR^eR^f$, —SH, and —$SR^g$, wherein $R^d$, $R^e$, $R^f$, $R^g$, and $R^g$, represent a $C_{1-6}$ alkyl group;
n is an integer of 1 to 4;
o is an integer of 1 or 2;
provided that when o is 2, the $R^8$ cannot be both OH.

The inventors have recognized that dental compositions, such as reinforced dental glass ionomer cements, are subject to deterioration during storage or after curing in the mouth of the patient. The inventors have further recognized that the deterioration includes hydrolytic degradation of the resin component conventionally containing hydrolyzable moieties. The inventors have then recognized that by using the polymerizable polyacidic polymer having repeating units of formula (I), the drawbacks of conventional dental compositions, such as resin reinforced glass ionomer cements known from the prior art, can be overcome.

The polymerizable pendant groups $R^1$ of the polymerizable polyacidic polymer having repeating units of formula (I) may react with a monomer having a polymerizable double bond, whereby a graft polymer is formed. The grafted side-chains may contain additional carboxylic acid groups which can take part in a cement reaction, thereby further increasing the strength of the cured composition.

Furthermore, owing to the polymerizable pendant groups $R^1$, the polymerizable polyacidic polymer having repeating units of formula (I) allows for crosslinking.

Besides, the polymerizable pendant groups $R^1$ of the polymerizable polyacidic polymer having repeating units of formula (I) are hydrolysis stable, since they do not contain functional groups susceptible to hydrolysis, such as ester groups.

Finally, the polymerizable polyacidic polymer having repeating units of formula (I) has acidic hydroxyl groups imparting an advantageously mild acidity which is however sufficient to render possible for example an acid-base reaction between a reactive glass powder and the polymerizable polyacidic polymer and/or between another component of an aqueous dental composition.

Further, the present invention provides a process for preparing a polymerizable polyacidic polymer, which comprises reacting a polyacidic polymer having repeating units of the following formula (IV):

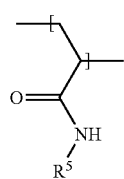
(IV)

wherein $R^5$ represents a group of the following formula (V):

(V)

with a compound of the following formula (VI)

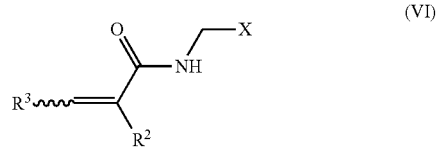
(VI)

wherein X is a leaving group, and
$R^2$ and $R^3$,
  which may be the same or different, independently represent a hydrogen atom, or a $C_{1-6}$ alkyl group which may be substituted with a carboxylic acid group.

With the present process, a polymerizable polyacidic polymer having repeating units of formula (I) can be efficiently obtained in high yields and high purity.

The present invention also provides an aqueous dental composition comprising the polymerizable polyacidic polymer having repeating units of formula (I).

Owing to the present polymerizable polyacidic polymer, a cured aqueous dental composition according to the present invention, preferably in the form of a glass ionomer composition, is hydrolysis-stable and has excellent mechanical properties. The polymerizable polyacidic polymer provides for crosslinking by a cement reaction, and owing to its acidic hydroxyl groups and optional carboxylic acid groups, adhesion to dental hard tissue may be improved.

Further, the present invention provides a use of the polymerizable polyacidic polymer having repeating units of formula (I) for the preparation of a dental composition.

Finally, the present invention provides an acrylic acid derivative copolymer which may be provided as a preferred starting material in the above mentioned process for preparing the polymerizable polyacidic polymer having repeating units of formula (I). Specifically, an acrylic acid derivative copolymer is provided which has repeating units of the following formulae (IV) and (III):

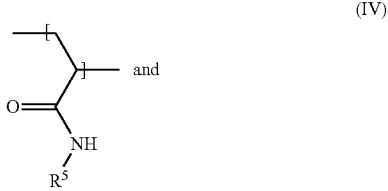
(IV)
and

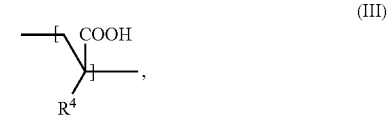
(III)

wherein $R^5$ represents a group of the following formula (V):

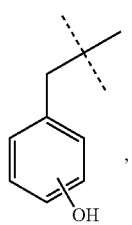

and $R^4$ represents a hydrogen atom, or a $C_{1-6}$ alkyl group which may be substituted with a carboxylic acid group, wherein the molar ratio between acrylic acid derivative repeating units of formula (III) and repeating units of formula (IV) ([formula (III)]/[formula (IV)]) is in the range of 1000:1 to 1:1.

DETAILED DESCRIPTION OF PREFERRED EMBODIMENTS

The term "polymerizable" as used with the term "polymerizable polyacidic polymer" means a polymer capable of combining by covalent bonding in an addition polymerization. The "polymerizable polyacidic polymer" may be combined with a crosslinker as well as e.g. with a monomer having polymerizable (carbon-carbon) double bond, to form graft polymers and/or crosslinked polymers when curing the aqueous dental composition.

The term "polyacidic" as used with the term "polymerizable polyacidic polymer" means that the polymer has a plurality of acidic groups, preferably carboxylic acid groups, which may participate in a cement reaction with a reactive glass. The carboxylic acid groups are preferably present in the backbone and derived from acrylic acid, methacrylic acid and/or itaconic acid. Additional acidity may be introduced by carboxylic acid groups in the group of formula (II) and carboxylic group(s) in the optional repeating unit of formula (III).

The Polymerizable Polyacidic Polymer

The polymerizable polyacidic polymer has repeating units of the following formula (I):

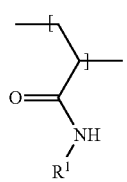

wherein $R^1$ represents a group of the following formula (II):

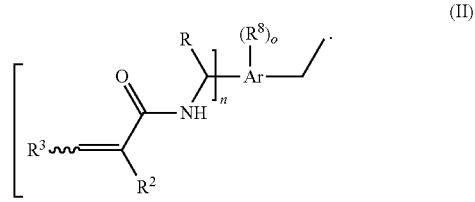

In the formulae depicted herein, the jagged/wavy bond indicates an unspecified configuration in the adjacent double bond ("Graphical Representation of Stereochemical Configuration" (IUPAC Recommendations 2006) Pure Appl. Chem., Vol. 78, No. 10, pp. 1897-1970, 2006). Specifically, the jagged bond indicates that $R^3$ may be in cis or trans configuration relative to the carbonyl group. Furthermore, in formula (II), the dashed line indicates the attachment of $R^1$ to the nitrogen of the amide moiety of the repeating unit of formula (I). In formula (V), the dashed line indicates the attachment of $R^5$ to the nitrogen of the amide moiety of the repeating unit of formula (IV).

The polymerizable polyacidic polymer having repeating units of formula (I) is water-soluble and is reactive with a particulate glass in a cement reaction, whereby the polymerizable polyacidic polymer has a polymer backbone and hydrolysis-stable pendant groups $R^1$ having one or more polymerizable carbon-carbon double bonds.

In formula (II), Ar is an aromatic group which may be further substituted. The aromatic group is not specifically limited and may be any organic aromatic group, i.e. a cyclic moiety which number of π-electrons equals 4n+2, where n is zero or any positive integer. Preferably, Ar is derived from an arene or heteroarene. An arene is a monoyclic or polycyclic aromatic hydrocarbon. A heteroarene is a heterocyclic compound formally derived from arenes by replacement of one or more methine (—C═) and/or vinylene (—CH═CH—) groups by trivalent or divalent heteroatoms, respectively, in such a way as to maintain the continuous π-electron system characteristic of aromatic systems and a number of out-of-plane π-electrons corresponding to the Hückel rule (4 n+2).

In case o+n is 2, Ar is preferably a $C_{6-14}$ arenetriyl or $C_{3-14}$ heteroarenetriyl group which may be further substituted by one or more substituents. In case o+n is 3, Ar is preferably a $C_{6-14}$ arenetetrayl or $C_{3-14}$ heteroarenetetrayl group which may be further substituted by one or more additional substituents. In case o+n is 4, Ar is preferably a $C_{6-14}$ arenepentayl or $C_{3-14}$ heteroarenepentayl group which may be further substituted by one or more additional substituents. In case o+n is 5, then Ar is preferably a $C_{6-14}$ arenehexayl or $C_{3-14}$ heteroarenehexayl group which may be further substituted by one or more additional substituent.

The additional substituents are selected from the group consisting of a straight chain or branched $C_1$ to $C_{10}$ alkyl group, a straight chain or branched $C_1$ to $C_{10}$ alkenyl group, —COOM, —PO$_3$M, —O—PO$_3$M$_2$ and —SO$_3$M, wherein M represents a hydrogen atom or a metal atom. More preferably, Ar is a $C_{6-10}$ arenetriyl or $C_{3-9}$ heteroarenetriyl group which may be substituted by one or more additional substituents selected from a straight chain or branched $C_1$ to $C_4$ alkyl group and a straight chain or branched $C_1$ to $C_4$ alkenyl group. Even more preferably, Ar is selected from a benzenetriyl group, a naphtalenetriyl group, a toluenetriyl group, a xylenetriyl group and a styrenetriyl group, and the heteroaryl group is a pyridinetriyl group. Yet even more preferably, Ar is a benzenetriyl group. Most preferably, Ar is a benzenetriyl group wherein a hydroxyl group is present in formula (II) in para-position to the methylene group linking $R^1$.

In formula (II), $R^2$ and $R^3$, which may be the same or different, independently represent a hydrogen atom, or a $C_{1-6}$ alkyl group which may be substituted with a carboxylic acid group. Preferably, $R^2$ and $R^3$, which may be the same or different, independently represent a hydrogen atom or a $C_{1-3}$ alkyl group. More preferably, $R^2$ represents a hydrogen atom or a methyl group, and $R^3$ represents a hydrogen atom. Most preferably, both $R^2$ and $R^3$ represent a hydrogen atom.

In formula (II), one or more R may be present depending on the value of n. The R may be the same or different when more than one R is present. R represents a hydrogen atom, a carboxylic acid group, a COOR$^a$ group, a CONHR$^b$ group, or a CONR$^c_2$ group. R$^a$, R$^b$, and R$^c$ represent a $C_{1-6}$ alkyl group. According to a preferred embodiment, R represents a hydrogen atom.

In formula (II), $R^8$ represents an electron donating group which activates the aryl group. Accordingly, each $R^8$ is directly bonded to a ring atom of the Ar group. $R^8$ may be a halogen atom or a group selected from —OH, —OR$^d$, —NR$^e$H, —NR$^e$R$^f$, —SH, and —SR$^g$, wherein R$^d$, R$^e$, R$^f$, R$^g$, and R$^g$, represent a $C_{1-6}$ alkyl group. Preferably, $R^8$ is a hydroxyl group. The halogen atom may be a fluorine atom, a chlorine atom, a bromine atom or an iodine atom. When o is 2, the $R^8$ cannot be both OH.

In formula (II), o is an integer of 1 or 2. Preferably, o is 1. In formula (II), n is an integer of 1 to 4. Preferably, n is an integer of 1 or 2. In formula (II), o+n is preferably 5 or less, more preferably 4 or less, in particular 3.

It is preferred that in formula (II), Ar is a phenyl group. Specifically, $R^1$ preferably represents a group of the following formula (II'):

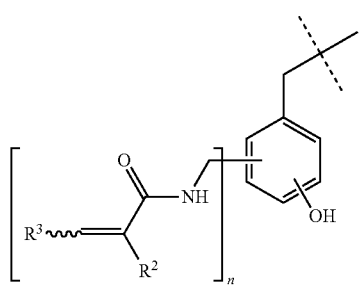

(II')

wherein $R^2$, $R^3$ and n are as defined as above.

It is particularly preferred that $R^1$ is a group of the following formula (II"$_a$) or (II"$_b$):

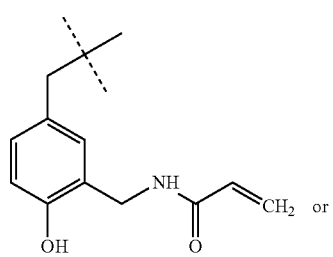

(II"$_a$)

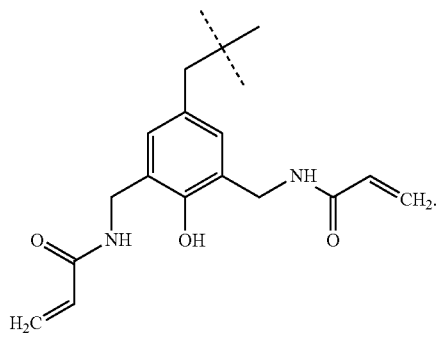

(II"$_b$)

Furthermore, it is preferred that the polymerizable polyacidic polymer having repeating units of formula (I) further comprises acidic repeating units of the following formula (III):

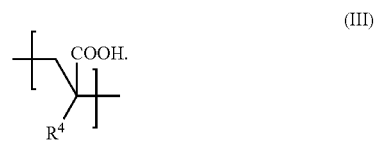

(III)

In formula (III), $R^4$ represents a hydrogen atom, or a $C_{1-6}$ alkyl group which may be substituted with a carboxylic acid group. Preferably, $R^4$ represents a hydrogen atom, or a $C_{1-3}$ alkyl group which may be substituted with a carboxylic acid group, more preferably $R^4$ represents a hydrogen atom or a methyl group. Most preferably, $R^4$ represents a hydrogen atom.

In the polymerizable polyacidic polymer having repeating units of formula (I), the molar ratio of repeating units of formula (III) and repeating units of formula (I) ([formula (III)]/[formula (I)]) is preferably in the range of 1000:1 to 1:1, more preferably 100:1 to 5:1, most preferably 50:1 to 10:1.

The polymerizable polyacidic polymer having repeating units of formula (I) preferably has a molecular weight $M_w$ in the range of 10,000 to 250,000, more preferably 20,000 to 150,000, most preferably 30,000 to 100,000.

The polymerizable polyacidic polymer having repeating units of formula (I) is hydrolysis stable, which means that it does not contain groups hydrolysing at pH 2.5 within one month when stored at a temperature of 50° C.

According to a particularly preferred embodiment, the polymerizable polyacidic polymer has repeating units of the following formula (I):

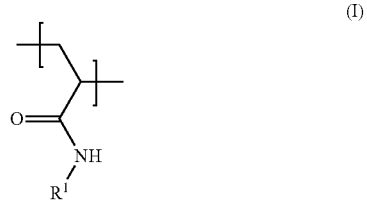

(I)

wherein $R^1$ represents a group of the following formula (II'):

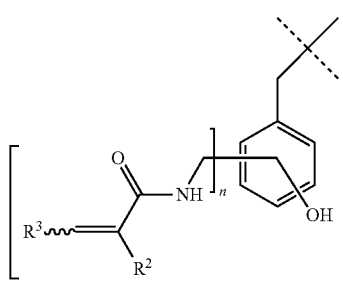
(II')

wherein
$R^2$ and $R^3$,
which may be the same or different, independently represent a hydrogen atom, or a $C_{1-4}$ alkyl group; preferably $R^2$ is a hydrogen atom or a methyl group and $R^3$ is a hydrogen atom, and
n is an integer of 1 to 3, preferably n is an integer of 1 or 2,
which polymerizable polyacidic polymer further comprises acidic repeating units of the following formula (III):

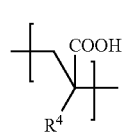
(III)

wherein
$R^4$ represents a hydrogen atom, or a $C_{1-4}$ alkyl group, preferably $R^4$ represents a hydrogen atom or a methyl group wherein the molar ratio of repeating units of formula (III) and repeating units of formula (I) ([formula (III)]/[formula (I)]) is in the range of 100:1 to 5:1, preferably 50:1 to 10:1, and the molecular weight $M_w$ is in the range of 20,000 to 150,000, preferably 30,000 to 100,000.

The Process for Preparing the Polymerizable Polyacidic Polymer

The process for preparing a polymerizable polyacidic polymer having repeating units of formula (I) comprises reacting a polyacidic polymer having repeating units of the following formula (IV):

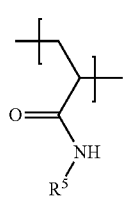
(IV)

wherein $R^5$ represents a group of the following formula (V):

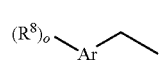
(V)

wherein
Ar is an aromatic group which may be further substituted;
$R^8$ represents a halogen atom or a group selected from —OH, —$OR^d$, —$NR^eH$, —$NR^eR^f$, —SH, and —$SR^g$, wherein $R^d$, $R^e$, $R^f$, $R^g$, and $R^g$, represent a $C_{1-6}$ alkyl group; and
o is an integer of 1 or 2, provided that when o is 2, the $R^8$ cannot be both OH,
with a compound of the following formula (VI)

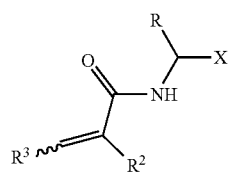
(VI)

wherein X is a leaving group, and
R, $R^2$ and $R^3$, which may be the same or different, independently represent a hydrogen atom, or a $C_{1-6}$ alkyl group which may be substituted with a carboxylic acid group.

In compound of formula (VI), leaving group X is preferably a leaving group susceptible to C—C bond-formation by means of electrophilic aromatic substitution. More preferably, leaving group X is selected from the group consisting of a fluorine atom, a chlorine atom, a bromine atom or a hydroxyl group. Most preferably, leaving group X is a hydroxyl group.

The reaction conditions for polymer analogous reaction of the polyacidic polymer having repeating units of the formula (IV) with a compound of formula (VI) are not particularly limited.

Preferably, the reaction is carried out in the presence of a solvent. More preferably, the solvent is water.

The reaction temperature for reacting the polyacidic polymer having repeating units of formula (IV) with a compound of formula (VI) is not particularly limited. Preferably, the reaction is carried out at a temperature of between 20 to 90° C. Most preferably, the reaction temperature is in the range of from 40 to 8000.

The reaction time for reacting the polyacidic polymer having repeating units of formula (IV) with a compound of formula (VI) is not particularly limited. Preferably, the reaction time is in the range of from 1 to 72 hours, most preferably 12 to 50 hours.

The molar ratio of polyacidic polymer having repeating units of formula (IV) to compound of formula (VI) is not particularly limited. Preferably, the molar ratio of polyacidic polymer having repeating units of formula (IV) to compound of formula (VI) is 1:5 to 1:1000, more preferably 1:100 to 1:800, most preferably 1:300 to 1:700.

Reacting of the polyacidic polymer having repeating units of formula (IV) with a compound of formula (VI) may be carried out in the presence of a catalyst, preferably a catalyst in the form of an organic or inorganic acid. More preferably, the catalyst is selected from the group consisting of hydrochloric acid, hydrobromic acid, hydrofluoric acid, phosphoric acid, sulphuric acid, sulfamic acid, oxalic acid and p-toluenesulfonic acid. Most preferably, the catalyst is hydrochloric acid or oxalic acid. The amount of catalyst may be selected from 0.01 to 100 mol %, preferably from 10 to 90 mol %, more preferably from 30 to 80 mol % based on the molar amount of the polyacidic polymer having repeating units of formula (IV) and compound of formula (VI).

The number n of groups of formula (II) in $R^1$ of the reaction product in the form of the polymerizable polyacidic polymer having repeating units of formula (I) may be set by suitably selecting the reaction conditions for reacting the polyacidic polymer having repeating units of formula (IV) with the compound of formula (VI). For example, for setting n=1, oxalic acid may be applied as the catalyst, and the reaction temperature is preferably within a range of 60 to 80° C. For setting n=2, hydrochloric acid may be applied as the catalyst, and the reaction temperature is preferably within a range of 35 to 55° C.

Furthermore, when reacting the polyacidic polymer having repeating units of formula (IV) with a compound of formula (VI), a stabilizer, polymerisation inhibitor, or antioxidant may be added which suppresses polymerisation and/or autoxidation of compound of formula (VI). Preferably, a stabilizer, polymerisation inhibitor, or antioxidant is selected from the group consisting of 3,5-di-tert-4-butylhydroxytoluene (BHT), 4-tert-butylcatechol, phenothioazine, tert-butyl hydroquinone (TBHQ) and hydroxytoluene. Most preferably, the antioxidant is BHT or 4-tert-butylcatechol. The amount of antioxidant may be selected from 0.001 to 2% and preferably from 0.02 to 0.5% based on the total weight of the polymerizable polyacidic polymer having repeating units of formula (IV)/compound of formula (VI)/solvent.

The reaction product obtained from reacting the polyacidic polymer having repeating units of formula (IV) with a compound of formula (VI) may be purified according to conventional methods. Preferably, the reaction product in the form of the polymerizable polyacidic polymer having repeating units of formula (I) is separated from the reaction mixture and purified by dialysis against water, more preferably the dialysis is carried out with a size exclusion of molecules having a molecular weight of up to 2000 g/mol. Owing to the purification by means of dialysis, or well-known polymer-chemically purification methods such as precipitation, liquid-liquid extraction. the polymerizable polyacidic polymer having repeating units of formula (I) is obtained in both high yields and purity.

According to a particularly preferred embodiment, the process for preparing a polymerizable polyacidic polymer having repeating units of formula (I) comprises reacting a polyacidic polymer having repeating units of the following formula (IV):

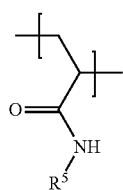

(IV)

wherein $R^5$ represents a group of the following formula (V):

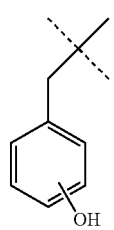

(V)

with a compound of the following formula (VIa)

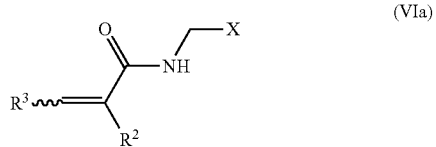

(VIa)

wherein X is a hydroxyl group, $R^2$ is a hydrogen atom or a methyl group, preferably a hydrogen atom, and $R^3$ is a hydrogen atom, in water as the solvent and in the presence of a catalyst selected from the group consisting of hydrochloric acid, hydrobromic acid, hydrofluoric acid, phosphoric acid, sulphuric acid, sulfamic acid, oxalic acid and p-toluenesulfonic acid, preferably the catalyst is hydrochloric acid or oxalic acid, wherein the amount of catalyst may be selected from 10 to 90 mol %, preferably from 30 to 80 mol % based on the molar amount of the polyacidic polymer having repeating units of formula (IV) and compound of formula (VIa), wherein the reaction temperature is in the range of from 40 to 80° C., and the molar ratio of polyacidic polymer having repeating units of formula (IV) to compound of formula (VIa) is 1:100 to 1:800, preferably 1:300 to 1:700.

A starting material in the form of the polyacidic polymer having repeating units of formula (IV) may be provided by polymerizing a monomer represented by the following formula (VII):

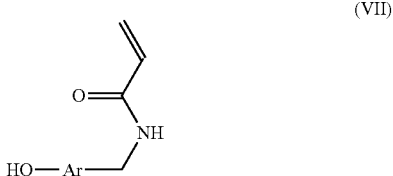

(VII)

wherein

Ar is an aromatic group as defined above for formula (II). Alternatively, the substitution pattern of the aromatic group may be adapted to the desired copolymer.

Preferably, the starting material in the form of the polyacidic polymer having repeating units of formula (IV) is an acrylic acid derivative copolymer having repeating units of formulae (IV) and (III) which may be obtained by copolymerizing a monomer represented by the following formula (VII):

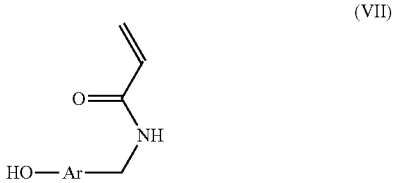

(VII)

wherein
Ar is an aromatic group as defined above,
with a monomer represented by the following formula (VIII)

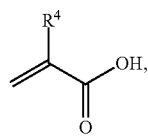

(VIII)

wherein $R^4$ is defined as above for formula (III).

The carboxylic acid group(s) optionally comprised in the monomer represented by formula (VII) and/or comprised in the monomer represented by formula (VIII) may optionally be protected.

The protecting group of an optionally protected carboxylic acid group is not particularly limited as long as it is a carboxyl-protecting group known to those of ordinary skill in the art of organic chemistry (cf. P. G. M. Wuts and T. W. Greene, Greene's Protective Groups in Organic Synthesis, 4th Edition, John Wiley and Sons Inc., 2007). Preferably, the carboxyl-protecting group is selected from a trialkylsilyl group, an alkyl group and an arylalkyl group. More preferably, the carboxyl-protecting group is selected from an alkyl group or an arylalkyl group. Most preferably, the carboxyl-protecting group is selected from a tert-butyl group and a benzyl group. In one preferred embodiment, the carboxyl-protecting group is a tert-butyl group.

The optionally protected carboxylic acid group(s) can be deprotected prior to polymerization or copolymerization of the monomer represented by formula (VII), concomitant thereto or subsequently thereto.

The conditions for deprotection of the optionally protected carboxylic acid group(s) are selected according to the protecting group used. Preferably, the protected carboxylic acid group(s) is/are deprotected by hydrogenolysis or treatment with acid or base.

If the deprotection of the optionally protected carboxylic acid group(s) is carried out concomitantly with polymerization or copolymerization of the monomer represented by formula (VII), it will be understood by a person skilled in the art that the deprotection conditions and the conditions for the polymerization or copolymerization have to be selected so that both reactions can proceed efficiently.

The reaction conditions for polymerizing or copolymerizing the monomer represented by formula (VII) are not particularly limited. Accordingly, it is possible to carry out the reaction in the presence or absence of a solvent. Preferably, the reaction is carried out in the presence of a solvent. A suitable solvent may be selected from the group of water, dimethyl formamide (DMF), tetrahydrofurane (THF), and dioxane. Preferably, the solvent is dioxane.

The reaction temperature for polymerizing or copolymerizing the monomer represented by formula (VII) is not particularly limited. Preferably, the reaction is carried out at a temperature of between −10° C. to the boiling point of the solvent. More preferably, the reaction temperature is in the range of from 0 to 110° C., even more preferably 40 to 100° C., most preferably 60 to 90° C.

The reaction time for polymerizing or copolymerizing the monomer represented by formula (VII) is not particularly limited. Preferably, the reaction time is in the range of from 10 minutes to 48 hours, more preferably 1 hour to 36 hours, even more preferably 2 to 24 hours, most preferably 3 to 12 hours.

The reaction for polymerizing or copolymerizing the monomer represented by formula (VII) is preferably carried out in the presence of a polymerization initiator. Preferably, the polymerization initiator is selected from azobisisobutyronitrile (AIBN), 2,2-azobis(2-amidinopropane)dihydrochloride, 2,2'-azobis(2-methylbutyronitrile), 2,2'-azobis(N,N'-dimethyleneisobutyramidine) dihydrochloride, and 4,4'-azobis(4-cyano pentanoic acid), most preferably, the polymerization initiator is AIBN. The amount of the polymerization initiator is not particularly limited. Suitably, the amount is in the range of from 0.001 to 5 mol % based on the total amount of the monomers.

The reaction for copolymerizing the monomer represented by formula (VII) and the monomer represented by formula (VIII) is preferably carried out by providing the monomer represented by the formula VII and the monomer represented by the formula VIII in the molar ratio ([formula (VII)]/[formula (VIII)]) in the range of 1000:1 to 1:1, more preferably 100:1 to 5:1, most preferably 50:1 to 10:1.

In the acrylic acid derivative copolymer having repeating units of formulae (IV) and (III), the molar ratio of repeating units of formula (III) and repeating units of formula (IV) ([formula (III)]/[formula (IV)]) is preferably in the range of 1000:1 to 1:1, more preferably 100:1 to 5:1, most preferably 50:1 to 10:1.

The reaction product obtained from polymerizing or copolymerizing the monomer represented by formula (VII) may be isolated by precipitation and filtration, or lyophilisation, preferably by precipitation and filtration. The reaction product may be purified according to conventional methods. It was surprisingly found that the reaction product can be obtained in both high yield and purity simply by dissolving and precipitating the reaction product, preferably twice. Hence, it can be dispensed with elaborate purification of the reaction product. For example, the crude reaction product may be dissolved in a suitable organic solvent, e.g. in dioxane, and precipitated by adding a suitable organic solvent, e.g. acetonitrile.

The acrylic acid derivative copolymer having repeating units of formulae (IV) and (III) may be a statistical copolymer, a random copolymer, an alternating copolymer, a block copolymer or a combination thereof. Preferably, it is a statistical copolymer.

Preferably, in the acrylic acid derivative copolymer having repeating units of formulae (IV) and (III), $R^1$ represents a group of the following formula (V'):

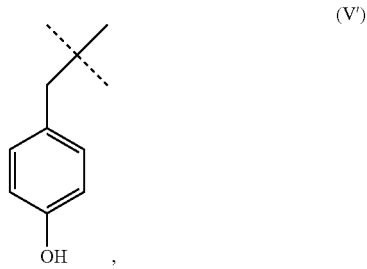

(V')

and
$R^4$ represents a hydrogen atom.

The monomer represented by the formula (VII) may be prepared by reacting a compound of the following formula (IX)

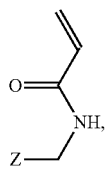

wherein Z is a leaving group,
with a compound of formula (X)

Ar—OH    (X), wherein Ar is an aromatic group as defined above for formula (II).

Preferably, leaving group Z of compound of formula (IX) is a leaving group susceptible to C—C bond-formation by means of electrophilic aromatic substitution. More preferably, leaving group Z is selected from the group consisting of a fluorine atom, a chlorine atom, a bromine atom or a hydroxyl group. Most preferably, leaving group Z is a hydroxyl group.

The reaction conditions for reacting the compound of formula (IX) with the compound of formula (X) are not particularly limited.

The reaction may be carried out in the absence or presence of a solvent, preferably in the presence of a solvent. The solvent is preferably selected from the group consisting of acetone, THF, ethyl acetate, chloroform, 1,2-dichlorethane. Most preferably, the solvent is acetone.

The reaction temperature for reacting the compound of formula (IX) with the compound of formula (X) is not particularly limited. Preferably, the reaction is carried out at a temperature of between −10 to 70° C. More preferably, the reaction temperature is in the range of from 10 to 60° C., most preferably from 30 to 50° C.

The reacting of the compound of formula (IX) with the compound of formula (X) may be carried out in the presence of a catalyst, preferably in the form of an organic or inorganic acid. More preferably, the catalyst is an inorganic Lewis acid, that is an inorganic electron acceptor. Even more preferably, the catalyst is selected from the group consisting of $AlCl_3$, $BF_3$, $FeCl_3$, $FeCl_2$, $FeBr_3$, $FeBr_2$, $FeSO_4$, $Fe_2(SO_4)_3$, $ZnCl_2$, $ZnBr_2$, $ZnSO_4$. Yet even more preferably, the catalyst is selected from the group consisting of $AlCl_3$, $BF_3$ and $FeCl_3$. Most preferably, the catalyst is $AlCl_3$. The amount of catalyst may be selected from 0.01 to 150 mol %, preferably from 30 to 130 mol %, more preferably from 60 to 120 mol %, most preferably from 90 to 110 mol % based on the molar amount of compound of formula (IX). Furthermore, when reacting the compound of formula (IX) with the compound of formula (X), an antioxidant may be added which suppresses polymerisation and/or autoxidation of compound of formula (IX). Preferably, the antioxidant is selected from the group consisting of 3,5-die-tert-4-butyl-hydroxytoluene (BHT), 4-tert-butylcatechol, phenothioazine, tert.-butyl hydroquinone (TBHQ) and hydroxytoluene. Most preferably, the antioxidant is phenothioazine. The amount of antioxidant may be selected from 0.001 to 2% and preferably from 0.02 to 0.5% based on the total weight of compound of formula (IX).

The reacting of the compound of formula (IX) with the compound of formula (X) is not particularly limited. Preferably, the reaction time is in the range of from 10 minutes to 48 hours, more preferably 1 hour to 36 hours, most preferably 2 to 24 hours.

The product obtained by reacting the compound of formula (IX) with the compound of formula (X) may be isolated from the crude reaction mixture by extraction with an organic solvent, preferably chloroform or dichloromethane. The product may be purified according to conventional methods, preferably by silica-gel column chromatography.

The Aqueous Dental Composition Comprising the Polymerizable Polyacidic Polymer

The aqueous dental composition comprising the polymerizable polyacidic polymer having repeating units of formula (I) may comprise one or more polymerizable polyacidic polymer(s) having repeating units of formula (I).

The aqueous dental composition comprising the polymerizable polyacidic polymer having repeating units of formula (I) preferably comprises a particulate glass filler. The aqueous dental composition may comprise one or more particulate glass filler(s).

Furthermore, it is preferred that the aqueous dental composition comprising the polymerizable polyacidic polymer having repeating units of formula (I) comprises a polymerizable monomer, a polymerisation initiator and optionally a stabilizer. The aqueous dental composition may comprise one or more polymerizable monomer(s), polymerisation initiator(s) and optional stabilizer(s).

It is particularly preferred that the aqueous dental composition comprising the polymerizable polyacidic polymer having repeating units of formula (I) is in the form of a dental glass ionomer composition.

Preferably, the aqueous dental glass ionomer composition comprises:
(A) The polymerizable polyacidic polymer having repeating units of formula (I),
(B) a particulate glass filler,
(C1) optionally a hydrolysis-stable, water-soluble monomer having one polymerizable double bond and optionally a carboxylic acid group; preferably, the monomer has a molecular weight of at most 200 Da;
(C2) optionally a hydrolysis-stable, water-soluble monomer having two or more polymerizable double bond and optionally a carboxylic acid group; and
(D) a polymerization initiator system.

In the following, sometimes components (A), (B), (C1), (C2) and (D) of the present aqueous dental glass ionomer composition are referred to by the terms "polymerizable polyacidic polymer according to (A)", "(particulate) glass filler according to (B)", "(hydrolysis-stable, water-soluble) monomer (having one polymerizable double bond) according to (C1)", "(hydrolysis-stable, water-soluble) monomer (having two or more polymerizable double bonds) according to (C2)" and "polymerization initiator system according to (D)" respectively.

The polymerizable polyacidic polymer according to (A) may be provided by the above described process for preparing the polymerizable polyacidic polymer having repeating units of formula (I).

The polymerizable polyacidic polymer according to (A) must be sufficient in number or percent by weight of hydroxyl groups and optional carboxylic acid groups to bring about the setting or curing reaction in the presence of the particulate glass filler according to (B). Preferably, the polymerizable polyacidic polymer according to (A) is present in the aqueous dental composition in an amount of from 5 to 80 percent by weight, more preferably 10 to 50 percent by weight, still more preferably 15 to 40 percent by weight, based on the total weight of the composition.

According to (B), the particulate glass filler comprises or consists of a reactive particulate glass filler.

The term "particulate glass filler" refers to a solid mixture of mainly metal oxides transformed by a thermal melt process into a glass and crushed by various processes. The glass is in particulate form. Moreover, the particulate glass filler may be surface modified, e.g. by silanation or acid treatment. Any conventional dental glass may be used for the purpose of the present invention. A reactive particulate glass filler is capable of reacting with a polymer containing acidic groups in a cement reaction. For example, a reactive particulate glass filler comprises glass containing cations having a valence of 2 or more which is adapted to be elutable by the polymer containing acidic groups.

Preferably, the particulate glass filler is a reactive particulate glass filler. Specific examples of reactive particulate glass fillers are selected from calcium alumino silicate glass, calcium alumino fluorosilicate glass, calcium aluminumfluoroborosilicate glass, strontium aluminosilicate glass, strontium aluminofluorosilicate glass, strontium aluminofluoroborosilicate glass. Further suitable reactive particulate glass fillers may be in the form of metal oxides such as zinc oxide and/or magnesium oxide, and/or in the form of ion-leachable glasses, e.g., as described in U.S. Pat. Nos. 3,655,605, 3,814,717, 4,143,018, 4,209,434, 4,360,605 and 4,376,835.

Preferably, the particulate glass filler according to (B) is a reactive particulate glass filler comprising:
1) 20 to 45% by weight of silica,
2) 20 to 40% by weight of alumina,
3) 20 to 40% by weight of strontium oxide,
4) 1 to 10% by weight of $P_2O_5$, and
5) 3 to 25% by weight of fluoride.

The present aqueous dental composition preferably comprises 20 to 90 percent by weight of the reactive particulate glass, more preferably 30 to 80 percent by weight, based on the total weight of the composition.

The particulate glass filler usually has an average particle size of from 0.005 to 100 μm, preferably of from 0.01 to 40 μm as measured, for example, by electron microscopy or by using a conventional laser diffraction particle sizing method as embodied by a MALVERN Mastersizer S or MALVERN Mastersizer 3000 apparatus.

The particulate glass filler may have a unimodal or multimodal (e.g., bimodal) particle size distribution, wherein a multimodal particulate glass filler represents a mixture of two or more particulate fractions having different average particle sizes.

The particulate glass filler may be a an agglomerated particulate glass which is obtainable by agglomerating a particulate glass in the presence of a modified polyacid and/or polymerizable (meth)acrylate resins. The particle size of the agglomerated particulate glass filler may be adjusted by suitable size-reduction processes such as milling.

The particulate glass filler may be surface modified by a component according to (A), (C1), (C2), and/or (D). In particular, the reactive particulate glass may be surface modified by one or more components of the polymerization initiator system (D) in order to avoid contact of the one or more components of the polymerization initiator system (D) with an acid under aqueous conditions.

The reactive particulate glass may alternatively or additionally be surface modified by a surface modifying agent. Preferably, the surface modifying agent is a silane. A silane provides a suitable hydrophobicity to the reactive particulate glass, which allows for an advantageous, homogeneous admixture with the organic components according to (A), (C1), (C2) and (D) of the aqueous dental glass ionomer composition.

According to (C1), the monomer having one polymerizable double bond is hydrolysis-stable and water-soluble. The aqueous dental composition according to the present invention may contain one or more monomer(s) according to (C1).

According to (C2), the monomer having one polymerizable double bond is hydrolysis-stable and water-soluble. The aqueous dental composition according to the present invention may contain one or more monomer(s) according to (C2).

The term "hydrolysis-stable" used in connection with the polymerizable polyacidic polymer according to (A) and the monomers according to (C1) and (C2) means that these compounds are stable to hydrolysis in an acidic medium, such as in a dental composition. In particular, the compounds according to (A), (C1) and (C2) do not contain groups which hydrolyze in aqueous media at pH 2.5 at a temperature of 50° C. within one month, such as ester groups.

The term "polymerizable double bond" as used herein in connection with the monomer according to (C1) and (C2) means any double bond capable of addition polymerization, in particular free radical polymerization, preferably a carbon-carbon double bond.

Further, the term "water-soluble" used in this connection means that at least 0.1 g, preferably 0.5 g of the monomer according to (C1) or (C2) dissolves in 100 g of water at 20° C.

The hydrolysis-stable, water-soluble monomers according to (C1) and (C2) are useful components of the aqueous dental glass ionomer composition according to the invention, since the monomers according to (C1) and (C2) polymerize with the polymerizable polymer according to (A) in the presence of the polymerization initiator system according to (D). Thereby, the monomers according to (C1) and (C2) may polymerize with itself and/or with the polymerizable pendant groups of the polymerizable compound according to (A). Hence, besides of the formation of a polymer formed of the monomer according to (C1) and/or (C2), there is a graft polymerization wherein monomer(s) according to (C1) and/or (C2) react with the polymerizable pendant groups $R^1$ of the polymerizable compound according to (A), whereby a graft polymer is formed. Furthermore, the graft side chains formed of the monomers according to (C1) and/or (C2) may additionally react with the pendant polymerizable groups of another polymerizable polymer according to (A), whereby a crosslinked polymer may be obtained.

In the following scheme, graft polymerisation by means of the monomer according to (C1) is depicted by way of example for the repeating unit of formula (I) of the polymerizable polyacidic polymer according to (A), wherein acrylic acid is merely exemplary selected as a monomer according to (C1). The letters "n" and "m" denote an integer of at least 1.

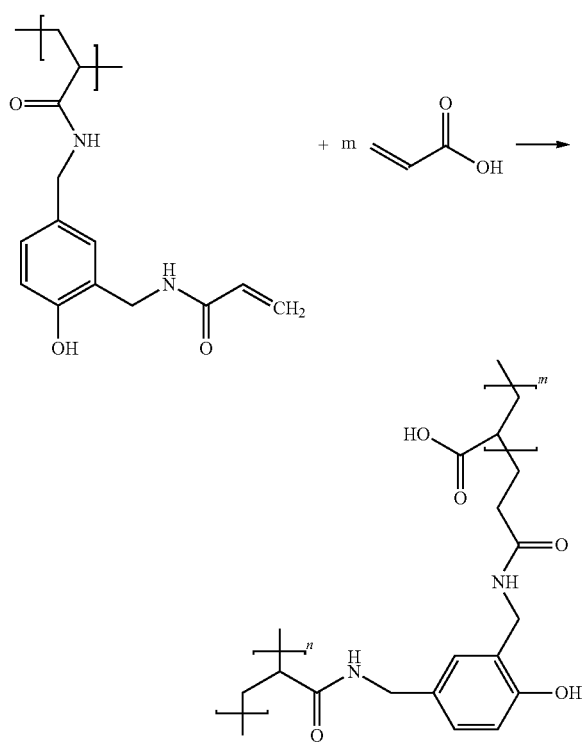

According to the present invention, one or a mixture of two or more monomers according to (C1) and/or (C2) may be used as component (C1) and/or (C2). A suitable monomer according to (C1) or (C2) is hydrolysis-stable. Specifically, a monomer according to (C1) or (C2) does not contain groups hydrolysing at pH 2.5 within one month at a temperature of 50° C. In particular, a suitable monomer according to (C1) or (C2) does not contain any ester group.

Furthermore, a suitable monomer according to (C1) contains one polymerizable double bond. A suitable monomer according to (C2) contains two or more polymerizable double bonds. Suitable polymerizable double bonds are carbon-carbon double bonds. In addition, the monomer according to (C1) or (C2) may contain a carboxylic acid group.

In a preferred embodiment, the monomer according to (C1) is a compound represented by the following formula (XI):

In formula (XI), $R^6$ is a hydrogen atom or a straight chain or branched $C_{1-3}$ alkyl group, and $R^7$ is a hydrogen atom or a straight-chain or branched $C_{1-6}$ alkyl group which may be substituted by a —COOH group. In formula (XI), the dotted line indicates that $R^6$ may be in either the cis or trans orientation. Preferably, $R^6$ is a hydrogen atom, and $R^7$ is a hydrogen atom or a $C_{1-3}$ alkyl group optionally substituted with a —COOH group. More preferably, $R^6$ is a hydrogen atom, and $R^7$ is a hydrogen atom or a methyl group substituted with a —COOH group, that is compound of formula (XI) is acrylic acid or itaconic acid. Most preferably, the compound of formula (XI) is acrylic acid.

Preferably, in formula (XI), residues $R^6$ and $R^7$ are selected with the proviso that the molecular weight of the monomer having one polymerizable double bond according to (C1) is at most 200 Da, more preferably at most 150 Da, most preferably at most 100 Da.

Furthermore, the hydrolysis-stable, water-soluble monomer having one polymerizable double bond may be 2-hydroxyethyl acrylamide (HEAA), N,N-dimethyl(meth)acrylamide, N,N-diethyl(meth)acrylamide, N,N-di-n-propyl(meth)acrylamide, and N-ethyl-N-methyl(meth)acrylamide. 2-Hydroxyethyl methacrylate (HEMA) and hydroxypropyl methacrylate may also be used in certain embodiments.

In a preferred embodiment, the monomer according to (C2) is a compound selected from bisacrylamide, bisallylacrylamide, and biscycloalkylacrylamide compounds.

The monomer according to (C1) or (C2) is preferably selected in view of a good processability and applicability of the final aqueous dental glass ionomer composition, in particular in terms of viscosity. Therefore, the viscosity of the monomer according to (C1) or (C2) is preferably in the range of 0.1 to 100 mPa·s, more preferably 0.3 to 50 mPa·s, even more preferably 0.5 to 25 mPa·s, yet even more preferably 0.8 to 10 mPa·s, in particular 0.9 to 3 mPa·s.

Monomers according to (C1) or (C2), comprising a carboxylic acid group are particularly advantageous, since such monomers introduce additional carboxylic acid groups into the acidic polymer in the aqueous dental glass ionomer composition, which can undergo a cement reaction resulting in a further improved setting or curing reaction in the presence of the reactive particulate glass according to (B).

Preferably, the monomer according to (C1) or (C2) is contained in the aqueous dental glass ionomer composition in an amount of from 0.1 to 20, more preferably 1 to 15 even more preferably 2 to 10 percent by weight based on the total weight of the aqueous dental glass ionomer composition. When the monomer according to (C1) or (C2) is absent, a long-term mechanical resistance may be low. On the other hand, when the amount monomer according to (C1) or (C2) exceeds 20 percent of weight, shrinkage of the dental glass ionomer cement obtained from the present aqueous dental glass ionomer composition may occur.

According to (D), as a polymerization initiator system, any compound or system capable of initiating a (co)polymerization reaction may be suitably used. The polymerization initiator according to (D) may be a photoinitiator or a redox initiator or a mixture thereof.

A suitable redox initiator comprises an reducing and oxidizing agents, which typically react with or otherwise cooperate with one another to produce free-radicals capable of initiating polymerization of polymerizable double bonds in components (A), (C1) and (C2) in a dark reaction, independent from the presence of light. The reducing and oxidizing agents are selected so that the polymerization initiator system is sufficiently storage-stable and free of undesirable colorization to permit storage and use under typical dental conditions. Moreover, the reducing and oxidizing agents are selected so that the polymerization initiator system is sufficiently miscible with the resin system to permit dissolution of the polymerization initiator system in the composition.

Useful reducing agents include ascorbic acid, ascorbic acid derivatives, and metal complexed ascorbic acid compounds as described in U.S. Pat. No. 5,501,727; amines, namely tertiary amines, such as 4-tert-butyl dimethylaniline;

aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine, salts of a dithionite or sulfite anion, and mixtures thereof.

Suitable oxidizing agents include persulfuric acid and salts thereof, such as ammonium, sodium, potassium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof. One or more different oxidizing agents or one or more different reducing agent may be used in the polymerization initiator system. Small quantities of transition metal compounds may also be added to accelerate the rate of redox cure. The reducing and oxidizing agents are present in amounts sufficient to permit an adequate free-radical reaction rate.

The reducing or oxidizing agents may be microencapsulated for enhancing shelf stability of the composition, and if necessary permitting packaging the reducing and oxidizing agents together (U.S. Pat. No. 5,154,762). Appropriate selection of an encapsulant may allow combination of the oxidizing and reducing agents and even of an acid-functional component and optional filler in a storage-stable state. Moreover, appropriate selection of a water-insoluble encapsulant allows combination of the reducing and oxidizing agents with the particulate reactive glass and water in a storage-stable state.

Suitable photoinitiators for polymerizing free radically photopolymerizable compositions may include binary and tertiary systems. Tertiary photoinitiators may include an iodonium salt, a photosensitizer, and an electron donor compound as described in U.S. Pat. No. 5,545,676. Suitable iodonium salts include the diaryl iodonium salts, e.g., diphenyliodonium chloride, diphenyliodonium hexafluorophosphate, diphenyl-iodonium tetrafluoroborate, and tolylcumyliodonium tetrakis(pentafluorophenyl)borate. Suitable photosensitizers are monoketones and diketones that absorb some light within a range of about 400 nm to about 520 nm (preferably, about 450 nm to about 500 nm). Particularly suitable compounds include alpha diketones that have some light absorption within a range of about 400 nm to about 520 nm (even more preferably, about 450 to about 500 nm). Examples include camphorquinone. Suitable electron donor compounds include substituted amines, e.g., ethyl dimethylaminobenzoate or dimethylamino benzonitrile.

Suitable photoinitiators may also include phosphine oxides typically having a functional wavelength range of about 380 nm to about 1200 nm. Examples of phosphine oxide free radical initiators with a functional wavelength range of about 380 nm to about 450 nm include acyl and bisacyl phosphine oxides such as those described in U.S. Pat. Nos. 4,298,738, 4,324,744 and 4,385,109 and EP 0 173 567. Specific examples of the acylphosphine oxides include 2,4,6-trimethylbenzoyldiphenylphosphine oxide, bis(2,4,6-trimethylbenzoyl)phenylphosphine oxide, dibenzoylphenylphosphine oxide, bis(2,6-dimethoxybenzoyl)phenylphosphine oxide, tris(2,4-dimethylbenzoyl)phosphine oxide, tris(2-methoxybenzoyl)phosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl-bis(2,6-dimethylphenyl) phosphonate, and 2,4,6-trimethylbenzoylethoxyphenylphosphine oxide. Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819), bis(2,6-dimethoxybenzoyl)-(2,4,4-trimethylpentyl) phosphine oxide (CGI 403), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700), a 1:1 mixture, by weight, of bis(2,4,6-trimethylbenzoyl)phenyl phosphine oxide and 2-hydroxy-2-methyl-1-phenylpropane-1-one (DAROCUR 4265), and ethyl 2,4,6-trimethylbenzylphenyl phosphinate (LUCIRIN LR8893X). Typically, the phosphine oxide initiator is present in the composition in catalytically effective amounts, such as from 0.1 percent by weight to 5.0 percent by weight, based on the total weight of the composition.

Examples of suitable aromatic tertiary amine include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, 4-N,N-dimethylaminobenzoic acid ethyl ester, 4-N,N-dimethylaminobenzoic acid methyl ester, 4-N,N-dimethylaminobenzoic acid n-butoxyethyl ester, 4-N,N-dimethylaminobenzoic acid 2-(methacryloyloxy) ethyl ester, 4-N,N-dimethylaminobenzophenone ethyl 4-(N,N-dimethylamino)benzoate and N,N-dimethylaminoethyl methacrylate. Examples of an aliphatic tertiary amine include trimethylamine, triethylamine, N-methyldiethanolamine, N-ethyldiethanolamine, N-n-butyldiethanolamine, N-lauryldiethanolamine, triethanolamine, 2-(dimethylamino) ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate.

The amine reducing agent may be present in the composition in an amount from 0.1 percent by weight to 5.0 percent by weight, based on the total weight of the composition.

The amount of active species of the polymerization initiator is not particularly limited. Suitably, the amount of polymerization initiator in the polymerization system according to (D) is in the range of from 0.001 to 5 mol % based on the total amount of the monomers.

The present aqueous dental composition provides a cured dental composition/cement. The cured dental composition/cement is preferably formed based on a reaction between (A) the polymerizable polyacidic polymer having repeating units of formula (I), (B) the particulate glass filler, (C) the hydrolysis-stable, water-soluble monomer having one polymerizable double bond and optionally a carboxylic acid group, and (D) the polymerization initiator system, in a cement reaction and a polyaddition reaction.

The term "curing" means the polymerization of functional oligomers and monomers, or even polymers, into a polymer network. Curing is the polymerization of unsaturated monomers or oligomers in the presence of crosslinking agents.

The term "curable" refers to a aqueous dental glass ionomer composition that will polymerize into a crosslinked polymer network when irradiated for example with actinic radiation such as ultraviolet (UV), visible, or infrared radiation, or when reacted with polymerisation initiators.

It was surprisingly found that when cured, the present dental composition in form of a glass ionomer composition has a particularly advantageous flexural strength is of at least 80 MPa as measured according to ISO 4049.

Optional Components of the Aqueous Dental Composition

It is preferred that the sum of the masses of the above described components (A) to (D) of the aqueous dental composition comprising the polymerizable polyacidic polymer having repeating units of formula (I) amounts to 100% by weight based on the total weight of the composition. However, this sum may also amount to less than 100%, preferably 90%, more preferably 80%, most preferably 70% by weight based on the total weight of the composition.

The remaining part of the aqueous dental composition which sum of components (A) to (D) amounts to less than 100% by weight based on the total weight of the composition may be constituted of further components. Such further components may be, for example, a crosslinker, a non-reactive glass filler and an inhibitor, which are described in the following.

Preferably, the aqueous dental composition according to the present invention further comprises:

(E) a polymerizable hydrolysis-stable crosslinker having at least two polymerizable carbon-carbon double bonds.

The term "hydrolysis-stable" used in connection with the crosslinker according to (E) has an analogous meaning as explained above for the monomer according to (C1)/(C2).

The aqueous dental composition according to the present invention may comprise one or more crosslinkers according to (E).

The crosslinker according to (E) may be an alkylenediol dimethylacrylate such as 1,3-butanediol dimethacrylate, 1,4-butanediol dimethacrylate, an alkylenediol divinyl ether such as 1,4-butanediol divinyl ether, di(ethylene glycol) dimethacrylate, di(ethylene glycol) divinyl ether, pentaerythritol diacrylate monostearate, ethylene glycol dimethacrylate, trimetylolpropane trimethacrylate, pentaerythritol triacrylate or triallyl ether, pentaerythritol tetraacrylate and trimetylolpropane triacrylate. The crosslinker according to (E) may also be 1,3-Bis(acrylamido)-N,N'-diethylpropane, N,N-Di(cyclopropyl acrylamido) propane.

Preferably, the crosslinker is a polymerizable compound of the following formula (XII), which is disclosed in EP2705827 and WO2014040729:

A''-L(B)$_{n'}$     (XII)

wherein

A'' is a group of the following formula (XIII')

(XIII)

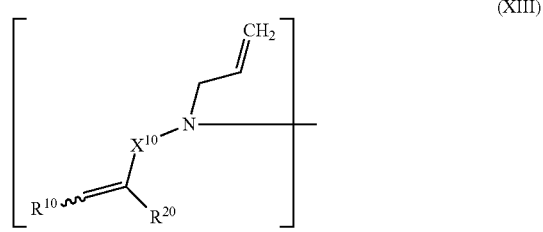

$X^{10}$ is CO, CS, CH$_2$, or a group $[X^{100}Z^{10}]_k$, wherein $X^{100}$ is an oxygen atom, a sulfur atom or NH, $Z^{10}$ is a straight chain or branched $C_{1-4}$ alkylene group, and k is an integer of from 1 to 10;

$R^{10}$ is a hydrogen atom,

—COOM$^{10}$, a straight chain or branched $C_{1-16}$ alkyl group which may be substituted by a $C_{3-6}$ cycloalkyl group, a $C_{6-14}$ aryl or $C_{3-14}$ heteroaryl group, —COOM$^{10}$, —PO$_3$M$^{10}$, —O—PO$_3$M$^{10}_2$ or —SO$_3$M$^{10}$, a $C_{3-6}$ cycloalkyl group which may be substituted by a $C_{1-16}$ alkyl group, a $C_{6-14}$ aryl or $C_{3-14}$ heteroaryl group, —COOM$^{10}$, —PO$_3$M$^{10}$, —O—PO$_3$M$^{10}_2$ or —SO$_3$M$^{10}$, a $C_{6-14}$ aryl or $C_{3-14}$ heteroaryl group which may be substituted by —COOM$^{10}$, —PO$_3$M$^{10}$, —O—PO$_3$M$^{10}_2$ or —SO$_3$M$^{10}$, $R^{20}$ is a hydrogen atom,

—COOM$^{10}$ a straight chain or branched $C_{1-16}$ alkyl group which may be substituted by a $C_{6-14}$ aryl or $C_{3-14}$ heteroaryl group, —COOM$^{10}$, —PO$_3$M$^{10}$, —O—PO$_3$M$^{10}_2$ and —SO$_3$M$^{10}$, a $C_{3-6}$ cycloalkyl group which may be substituted by a $C_{1-16}$ alkyl group, a $C_{6-14}$ aryl or $C_{3-14}$ heteroaryl group, —COOM$^{10}$, —PO$_3$M$^{10}$, —O—PO$_3$M$^{10}_2$ or —SO$_3$M$^{10}$, or a $C_{6-14}$ aryl or $C_{3-14}$ heteroaryl group which may be substituted by —COOM$^{10}$, —PO$_3$M$^{10}$, —O—PO$_3$M$^{10}_2$ and —SO$_3$M$^{10}$, L is a single bond or a linker group;

B independently is i) a group according to the definition of A'', ii) a group of the following formula (XIV)

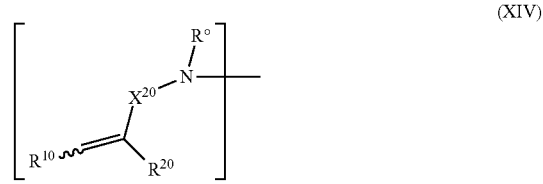

(XIV)

wherein $X^{20}$ independently has the same meaning as defined for $X^1$ in formula (XIII), $R^{10}$ and $R^{20}$ are independent from each other and independently have the same meaning as defined for formula (XIII), $R^o$ is a hydrogen atom, a straight chain or branched $C_{1-16}$ alkyl group which may be substituted by a $C_{3-6}$ cycloalkyl group, a $C_{6-14}$ aryl or $C_{3-14}$ heteroaryl group, —COOM$^{10}$, —PO$_3$M$^{10}$, —O—PO$_3$M$^{10}_2$ or —SO$_3$M$^{10}$, a $C_{3-6}$ cycloalkyl group which may be substituted by a $C_{1-6}$ alkyl group, a $C_{6-14}$ aryl or $C_{3-14}$ heteroaryl group, —COOM$^{10}$, —PO$_3$M$^{10}$, —O—PO$_3$M$^{10}_2$ or —SO$_3$M$^{10}$, a $C_{6-14}$ aryl group which may be substituted by —COOM$^{10}$, —PO$_3$M$^{10}$, —O—PO$_3$M$^{10}_2$ or —SO$_3$M$^{10}$, iii) a group of the following formula (XV)

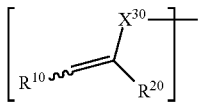

wherein
$X^{30}$ is CO, —$CH_2CO$—, CS, or —$CH_2CS$—,
$R^{10}$ and $R^{20}$ which are independent from each other and independently have the same meaning as defined for formula (XIII), or
iv) a group $[X^{40}Z^{200}]_pE$,
wherein
$Z^{200}$ is a straight chain or branched $C_{1-4}$ alkylene group,
$X^{40}$ is an oxygen atom, a sulfur atom or NH,
E is a hydrogen atom,
  $PO_3M_2$,
  a straight chain or branched $C_{1-16}$ alkyl group which may be substituted by a $C_{3-6}$ cycloalkyl group, a $C_{6-14}$ aryl or $C_{3-14}$ heteroaryl group, —$COOM^{10}$, —$PO_3M^{10}$, —O—$PO_3M^{10}_2$ or —$SO_3M^{10}$,
  a $C_{3-6}$ cycloalkyl group which may be substituted by a $C_{1-16}$ alkyl group, a $C_{6-14}$ aryl or $C_{3-14}$ heteroaryl group, —$COOM^{10}$, —$PO_3M^{10}$, —O—$PO_3M^{10}_2$ or —$SO_3M^{10}$,
  a $C_{6-14}$ aryl or $C_{3-14}$ heteroaryl group which may be substituted by —$COOM^{10}$, —$PO_3M^{10}$, —O—$PO_3M^{10}_2$ or —$SO_3M^{10}$, and
p is an integer of from 1 to 10;
and
n' is an integer of from 1 to 4;
wherein $M^{10}$ which are independent from each other each represent a hydrogen atom or a metal atom. Preferably, when L is a single bond, B cannot be a group according to the definition of A" or a group of the formula (XIV).
The following groups are preferred groups of formula (XIII), wherein M is a hydrogen atom or a metal atom:

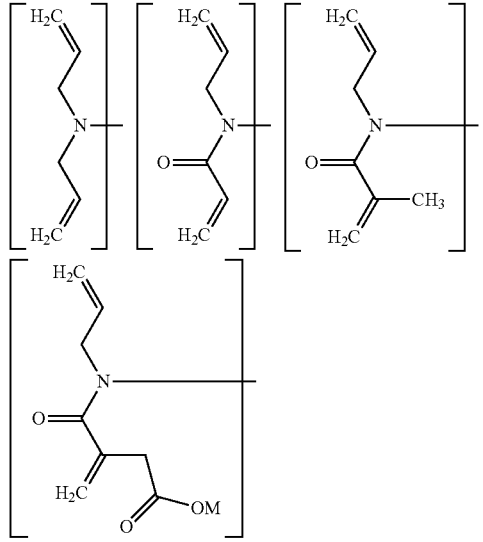

For L, the linker group may be a hydrocarbon group which may be aliphatic and/or aromatic and preferably has 1 to 45 carbon atoms. The hydrocarbon group may be substituted by 1 to 6 $C_{1-4}$ alkyl groups. Specific examples of the alkyl groups are methyl, ethyl, n-propyl, i-propyl, n-butyl, i-butyl or tert.-butyl. In a preferred embodiment, for L, the hydrocarbon group of the linker group may contain 1 to 5 heteroatoms selected from oxygen, nitrogen and sulphur. The oxygen atoms and sulphur atoms in the hydrocarbon group may be in the form of ether or thioether bonds, keto or sulfoxide groups, carboxylic acid or sulfonic acid groups, hydroxyl or thiol groups. Ester or thioester groups are not preferred in moiety L in view of hydrolysis stability of the polymerizable monomer. In case of an aliphatic group, L may be a straight chain or branched chain $C_1$ to $C_{18}$ alkylene group, $C_2$ to $C_{18}$ alkenylene group, $C_3$ to $C_{18}$ cycloalkylene or cycloalkenylene group. In case of an aromatic group, L may be an $C_4$ to $C_{18}$ arylene or heteroarylene group. Specifically, L may be a divalent substituted or unsubstituted $C_1$ to $C_{20}$ alkylene group, substituted or unsubstituted $C_{6-14}$ arylene group, substituted or unsubstituted $C_3$ to $C_{20}$ cycloalkylene group, substituted or unsubstituted $C_7$ to $C_{20}$ arylenealkylenearylene group.

According to a preferred embodiment, L represents a saturated or unsaturated aliphatic $C_{2-20}$ hydrocarbon chain which may contain 2 to 4 oxygen atoms or nitrogen atoms, and which may be substituted by 1 to 6 $C_{1-4}$ alkyl groups, or L may be a substituted or unsubstituted $C_7$ to $C_{20}$ arylenealkylenearylene group which may be substituted by 1 to 6 $C_{1-4}$ alkyl groups.

Preferably, the linker group is a divalent $C_{1-12}$ hydrocarbon group. The divalent $C_{1-12}$ hydrocarbon group may contain 1 to 3 carbonyl groups or heteroatoms selected from oxygen, nitrogen and sulfur. Moreover, the $C_{1-12}$ hydrocarbon group may be substituted by a hydroxyl group, a $C_{6-14}$ aryl group, —COOM, —$PO_3M$, —O—$PO_3M_2$ or —$SO_3M$, wherein M is a hydrogen atom or a metal atom. Specific examples of a divalent $C_{1-12}$ hydrocarbon group are a straight chain or branched $C_{1-12}$ alkylene group such as a methylene, ethylene, propylene or butylene group, and straight chain or branched $C_{2-12}$ alkenylene group such as a ethenylene, propenylene or butenylene group, which groups may be substituted by a hydroxyl group, a $C_{6-14}$ aryl group, —COOM, —$PO_3M$, —O—$PO_3M_2$ or —$SO_3M$.

Preferred divalent linker groups may be selected from methylene, ethylene, propylene, butylene, ethenylene, propenylene (prop-1-enylene or prop-2-enylene) or butenylene (but-1-enylene, but-2-enylene) and the following divalent groups:

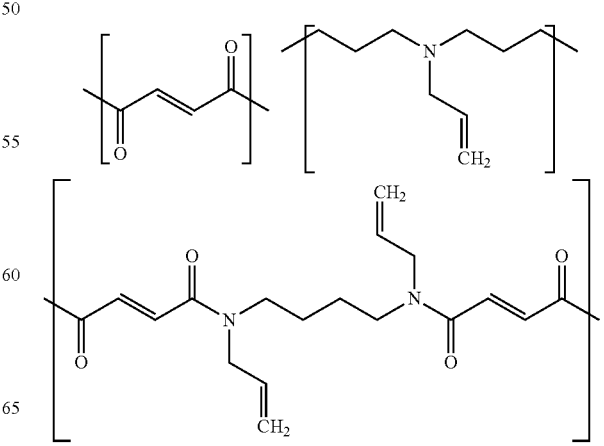

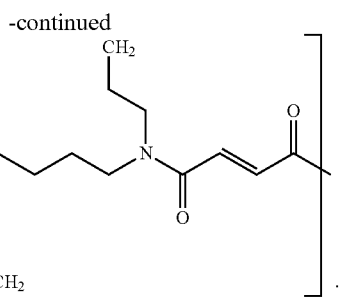

Most preferably, the divalent linker group L is propylene or but-2-enylene

Particularly preferred crosslinkers are N,N'-diallyl-1,4-bisacrylamido-(2E)-but-2-en (BAABE), and N,N'-diethyl-1,3-bisacrylamido-propan (BADEP).

The present aqueous dental composition may further comprise (F) a non-reactive filler, which does not undergo a cement reaction with the polymerizable polyacidic polymer. A non-reactive filler is not capable of reacting with a polymer containing acidic groups in a cement reaction. The term "non-reactive glass filler" as used herein means any filler other than the above described reactive glass filler.

A non-reactive filler according to (F) may be included in the present aqueous dental glass composition for changing the appearance of the composition, for controlling viscosity of the composition, for further improving mechanical strength of a dental glass ionomer cement obtained from the composition, and e.g. for imparting radiopacity. The non-reactive filler should be non-toxic and suitable for use in the mouth or for paste-paste delivery.

The non-reactive filler according to (F) may be in the form of an inorganic or organic material. For example, suitable non-reactive inorganic fillers may be quartz, nitrides such as silicon nitride, colloidal silica, submicron silica such as pyrogenic silicas, colloidal zirconia, feldspar, borosilicate glass, kaolin, talc or a metallic powder comprising one or more metals or metal alloys.

Examples of suitable organic non-reactive fillers include filled or unfilled particulate polycarbonates or polyepoxides, or a crosslinked organic material which is insoluble in the polymerizable polymer according to (A) comprised in the present aqueous dental composition, and is optionally filled with inorganic filler. Preferably, the surface of the organic non-reactive non-glass filler particles is treated with a coupling agent in order to enhance the bond between the filler and the matrix. Suitable coupling agents include silane compounds such as gamma-methacryloxypropyltrimethoxysilane, gamma-mercaptopropyltriethoxysilane and gamma-aminopropyltrimethoxysilane.

The non-reactive filler may have a unimodal or polymodal (e.g., bimodal) particle size distribution, wherein the particulate filler preferably has an average particle size of from 0.005 to 100 μm, preferably of from 0.01 to 40 μm. The particle size may be measured, for example, by electron microscopy or by using a conventional laser diffraction particle sizing method as embodied by a MALVERN Mastersizer S or MALVERN Mastersizer 3000 apparatus. The particulate filler may be a multimodal particulate non-reactive filler representing a mixture of two or more particulate fractions having different average particle sizes. The particulate reactive filler may also be a mixture of particles of different chemical composition. The particulate non-reactive non-glass filler may be surface modified by a surface modifying agent.

The aqueous dental composition according to the present invention may, besides of the optional crosslinker and non-reactive filler, comprise additional optional components.

For example, the aqueous dental composition according to the present invention may also include further components to improve the radio-opacity, such as $CaWO_4$, $ZrO_2$, $YF_3$ or to increase the fluoride release such as $YF_3$.

For example, the aqueous dental composition according to the present invention may also include a modifying agent such as tartaric acid. Such modifying agent provides for adjusting the working time and a setting time of the glass ionomer cement reaction, respectively, when preparing the cement as described in U.S. Pat. Nos. 4,089,830, 4,209,434, 4,317,681 and 4,374,936. In general, an increase in working time results in an increase in setting time as well.

The "working time" is the time between the beginning of the setting reaction when the polymer and modified particulate reactive filler are combined in the presence of water, and the time the setting reaction proceeds to the point when it is no longer practical to perform further physical work upon the system, e.g. spatulate it or reshape it, for its intended dental or medical application.

The "setting time" is the time measured from the beginning of the setting reaction in a restoration to the time sufficient hardening has occurred to allow subsequent clinical or surgical procedures to be performed on the surface of the restoration.

In a setting reaction, due to the presence of polymerizable double bonds, a polymerization reaction takes place.

The aqueous dental composition according to the present invention may contain further components such as solvents, pigments, nonvitreous fillers, free radical scavengers, polymerization inhibitors, reactive and nonreactive diluents e.g. bisacrylamides such as N,N'-diethyl-1,3-bisacrylamido-propan (BADEP), 1,3-bisacrylamido-propan (BAP), and 1,3-bisacrylamido-2-ethyl-propan (BAPEN), surfactants (such as to enhance solubility of an inhibitor e. g., polyoxyethylene), coupling agents to enhance reactivity of fillers e.g., 3-(trimethoxysilyl) propyl methacrylate, and rheology modifiers.

Suitable solvents or nonreactive diluents include alcohols such as ethanol and propanol.

Suitable reactive diluents are alpha,beta unsaturated monomers for providing altered properties such as toughness, adhesion, and set time. Such alpha,beta-unsaturated monomers may be acrylates and methacrylates such as methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bisphenol A ("bis-GMA"), glycerol mono- and di-acrylate, glycerol mono- and di-methacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)]propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, and 2,2'-bis[3(4-phenoxy)-2-hydroxypropane-1-acryalte]propane, may be mentioned. Other suitable examples of polymerizable components are isopropenyl oxazoline, vinyl azalactone, vinyl pyrrolidone, styrene, divinylbenzene, urethane acrylates or methacrylates, epoxy acrylates or methacrylates and polyol acrylates or methacrylates. Mixtures of alpha,beta-unsaturated monomers can be added if desired. Preferably, the mixed but unset dental compositions of the invention will contain a combined weight of about 0.5 to about 40%, more preferably about 1 to about 30%, and most preferably about 5 to 20% water, solvents, diluents and alpha,beta-unsaturated monomers, based on the total weight (including such water, solvents, diluents and alpha,beta-unsaturated monomers) of the mixed but unset aqueous dental glass ionomer composition components.

An example of a suitable free radical scavenger is 4-methoxyphenol.

An example of a suitable inhibitor is tert.-butyl hydroquinone (TBHQ), hydroxytoluene or butylated hydroxytoluene (BHT).

The term "inhibitor" as used herein means any compound capable of preventing polymerizable compounds contained in the aqueous dental composition from spontaneous polymerization during storage. However, the inhibitor does not disturb or prevent intended polymerisation curing of the aqueous dental composition during application.

The aqueous dental composition according to the present invention may contain one or more inhibitors.

Particularly preferred inhibitors are compounds of the following formula (XVI) and/or (XVII):

(XVI)

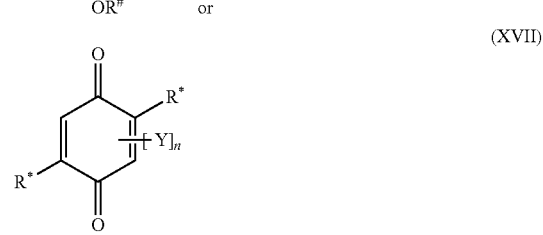

(XVII)

wherein the R*, which may be the same or different, independently represent a branched $C_{3-8}$ alkyl group or alkenyl or a $C_{3-8}$ cycloalkyl or cycloalkenyl group, $R^\#$ represents a $C_{1-6}$ alkyl or $C_{2-6}$ alkenyl group, or a $C_{1-6}$ fluoroalkyl or $C_{2-6}$ fluoroalkenyl group, Y represents a group selected from a $C_{1-8}$ alkyl group or a $C_{3-8}$ cycloalkyl group, and n is 0, 1 or 2.

It was surprisingly found that the class of inhibitors of formula (XVI) and/or (XVII) provides for full or at least substantial avoidance of discoloration upon storage and/or during photocuring. In particular, this class of inhibitors provides for a surprising stabilizing effect in an acidic aqueous mixture so that an aqueous dental composition having a pH of at most 7 may be provided which has no or substantially no discoloration upon storage and an excellent storage stability due to an improved resistance against premature polymerization.

More preferably, the inhibitor is a compound of formula (XVI) and/or (XVII) wherein the R*, which may be the same or different, independently represent a branched $C_{3-8}$ alkyl group or a $C_{3-8}$ cycloalkyl group, and $R^\#$ represents a $C_{1-6}$ alkyl group or a $C_{1-6}$ fluoroalkyl group, and n is 0 or 1. Even more preferably, the inhibitor is a compound of formula (XVI) and/or (XVII) wherein the R*, which may be the same or different, independently represent a branched $C_{3-8}$ alkyl group and $R^\#$ represents a $C_{1-6}$ alkyl group, and n is 0. Most preferably, the inhibitor is a compound of the following formulae (XVIa), (XVIb) or (XVIIa):

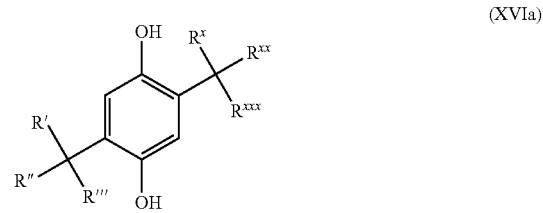

(XVIa)

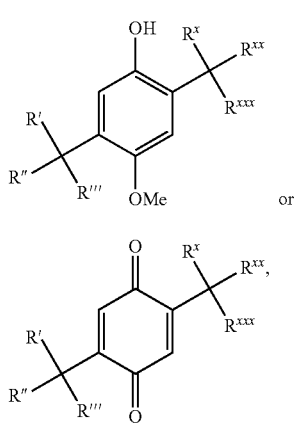

(XVIb)

(XVIc)

wherein R', R'', R''', $R^x$, $R^{xx}$ and $R^{xxx}$, which may be the same or different, independently represent a methyl or an ethyl group. It is particularly preferred that the inhibitor of formulae (XVIa), (XVIb) or (XVIIa) is a compound of the following formulae:

(DTBHQ),

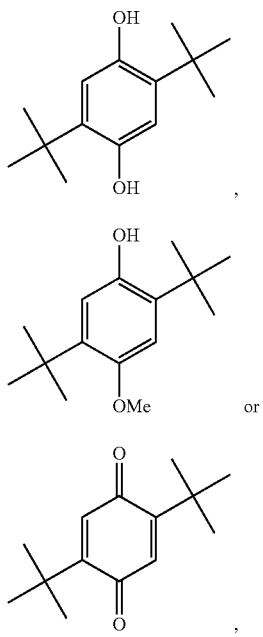

(DTBHQ)

(DTBMP)

(DTBBQ)

preferably DTBHQ.

The aqueous dental composition according to the invention contains the inhibitor in an amount of 0.001 to 1 percent by weight, preferably 0.005 to 0.8 percent by weight based on the total weight of the composition. When the amount of the inhibitor is below the above indicated lower limit of 0.001, then storage stability of the aqueous dental composition might be insufficient, since the amount of inhibitor is too small to provide a stabilizing effect. However, when the amount of inhibitor is above the maximum threshold of 1 percent by weight, then the applicability of the aqueous dental composition might be negatively affected, since higher amounts of inhibitor may disturb or even substantially prevent intended polymerisation curing of the aqueous dental composition during application.

According to a particularly preferred embodiment, the aqueous dental composition according to the present invention is an aqueous dental glass ionomer composition comprising:

(A) the polymerizable polyacidic polymer having repeating units of formula (I), preferably the particularly preferred embodiment thereof described above, (B) a particulate glass filler in the form of a reactive particulate glass filler comprising:
　1) 20 to 45% by weight of silica,
　2) 20 to 40% by weight of alumina,
　3) 20 to 40% by weight of strontium oxide,
　4) 1 to 10% by weight of $P_2O_5$, and
　5) 3 to 25% by weight of fluoride.

(C) a hydrolysis-stable, water-soluble monomer represented by the following formula (XI):

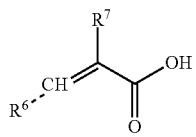

(XI)

wherein $R^6$ is a hydrogen atom, and $R^7$ is a hydrogen atom or a $C_{1-3}$ alkyl group optionally substituted with a —COOH group, preferably, $R^6$ is a hydrogen atom, and $R^7$ is a hydrogen atom or a methyl group, (D) a polymerization initiator system comprising an alpha diketone photoinitiator and an electron donor compound, preferably in an electron donor compound in the form of a substituted amine, and (E) a polymerizable, hydrolysis-stable crosslinker A''-L-B (XII)
wherein
A'' is a group of the following formula (XIII')

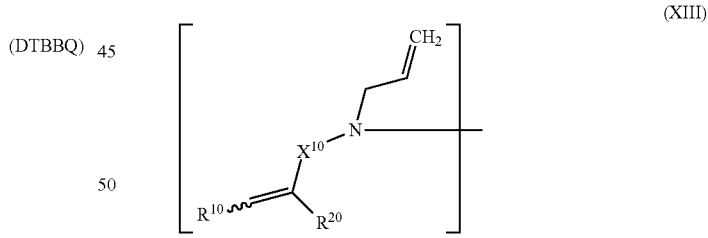

(XIII)

$X^{10}$ is CO;
$R^{10}$ is a hydrogen atom, —$COOM^{10}$, or a straight chain or branched $C_{1-4}$ alkyl group, preferably $R^{10}$ is a hydrogen atom or a methyl group, more preferably a hydrogen atom,
$R^{20}$ is a hydrogen atom, —$COOM^{10}$, a straight chain or branched $C_{1-4}$ alkyl group, preferably $R^{20}$ is a hydrogen atom or a methyl group, more preferably a hydrogen atom,
L is a straight chain or branched $C_{1-12}$ alkylene group or a straight chain or branched $C_{2-12}$ alkenylene group,
B is a group according to the definition of A'';
wherein $M^{10}$ which are independent from each other each represent a hydrogen atom or a metal atom.

Use of the Polymerizable Polyacidic Polymer Having Repeating Units of Formula (I)

The polymerizable polyacidic polymer having repeating units of formula (I) may be used for the preparation of an aqueous dental composition, preferably for the preparation of an aqueous dental composition as described above, more preferably for the preparation of a aqueous dental glass ionomer composition as described above.

The dental composition may be a dental material to be used in the oral cavity. Dental compositions for use according to the present inventive concept represent useful restorative and filling materials, luting cements, adhesive cements, base or orthodontic cements, cavity liners and bases, pit and fissure sealants.

The invention will now be further illustrated by the following Examples.

EXAMPLES

Example 1

Preparation of Poly[(N-(4-hydroxybenzyl)acrylamide)-co-(acrylic acid)]

1.) Preparation of N-(4-hydroxybenzyl)acrylamide

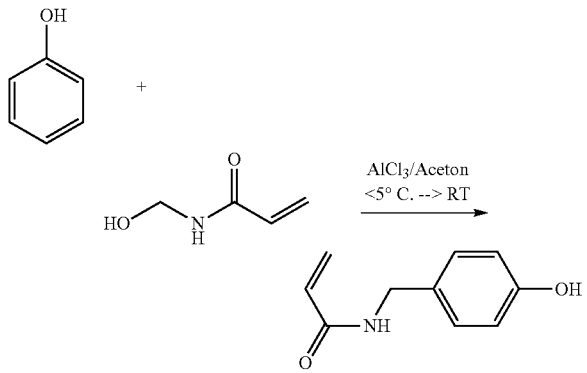

To a stirred solution of N-(hydroxymethyl)acrylamide (17.19 g, 170 mmol) and phenothiazine (10 mg) in acetone (80 mL) was added aluminum chloride (22.7 g, 170 mmol) while cooling in an ice bath (0-5° C.). The reaction mixture was then slowly heated to 40° C. and phenol (20.0 g, 212 mmol) dissolved in Acetone (150 mL) were added dropwise. After complete addition, the reaction mixture was stirred at 40° C. for 16 h. After cooling to 5° C., the reaction mixture was diluted with 100 mL water, stirred for 30 min and extracted with dichloromethane for at least three times. The combined organic layers were dried with magnesium sulfate and evaporated by rotary evaporator under reduced pressure to give the crude product. The crude product was purified by column chromatography (acetone/dichloromethane 1:4) over silica-gel to furnish the pure product.

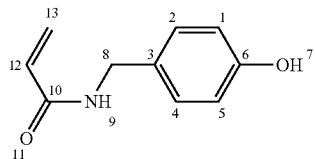

Yield: 7.9 g (26%)

Mp.: 103° C.

IR v [cm$^{-1}$]: 3302 (m), 3094 (m), 3020 (m), 2934 (m), 2809 (m), 2684 (w), 2605 (w), 2501 (w), 1654 (m), 1612 (m), 1591 (m), 1558 (s), 1513 (s), 1459 (m), 1432 (m), 1411 (m), 1379 (w), 1356 (m), 1321 (m), 1250 (s), 1228 (s), 1168 (m), 1105 (m), 1068 (m), 1044 (w), 1018 (w), 998 (w), 975 (w), 968 (m), 959 (w), 930 (w), 846 (w), 831 (s), 803 (m), 771 (m), 719 (m), 702 (m), 650 (w), 642 (w), 585 (s), 511 (w), 490 (m).

$^1$H-NMR [ppm]: (300 MHz, DMSO-d$_6$): δ 9.30 (s, 1H, H7), 8.52-8.41 (m, 1H), 7.13-7.02 (m, 2H, 2, H4), 6.78-6.66 (m, 2H, H1, 5), 6.27 (dd, J=17.1, 10.0 Hz, 1H, H13"), 6.11 (dd, J=17.1, 2.4 Hz, 1H, H12), 5.60 (dd, J=10.0, 2.4 Hz, 1H, H13"), 4.23 (d, J=5.8 Hz, 2H, H8).

$^{13}$C-NMR [ppm]: (75 MHz, CDCl$_3$): δ 164.35, 156.30, 131.73, 129.32, 128.75, 125.16, 115.02, 41.73.

MS (GC/MS (EI)): 177 m/z

Elemental analysis: calculated C, 67.78, H, 6.26, N, 7.90, found C, 67.89, H, 6.45, N, 7.79.

2.) Copolymerization of N-(4-hydroxybenzyl)acrylamide and acrylic acid

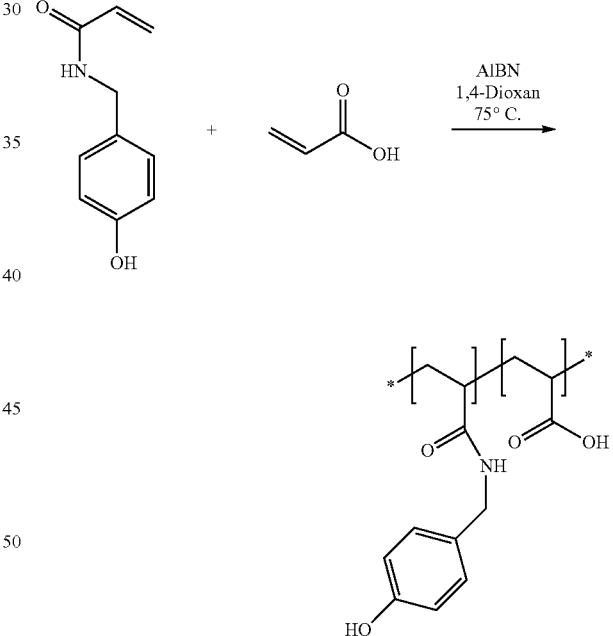

Acrylic acid (22.8 g, 316 mmol), N-(4-hydroxybenzyl)acrylamide (1.7 g, 9.6 mmol) and 2,2'-azobis(2-methylpropionitrile) (AIBN, 2 mol-%, 1.07 g, 6.5 mmol) were dissolved in dioxane (125 mL) and the solution was purged with nitrogen for 30 min. The solution was placed in a pre-heated oil bath (75° C.) and stirred for four hours at 75° C. After cooling to room temperature, the polymer was precipitated by adding the reaction solution to 1 L acetonitrile. The mixture was filtered and the polymer was dissolved in dioxane and precipitated again. The dissolution/precipitation step was repeated twice to give the pure polymer.

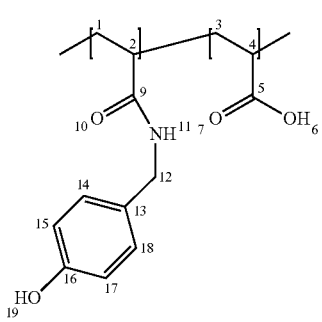

Yield: 17.16 g (70%)

IR ν [cm$^{1}$]: 3150 (br, m), 2944 (m), 1704 (s), 1549 (w), 1517 (w), 1451 (m), 1408 (m), 1231 (s), 1169 (s), 1113 (w), 801 (s), 620 (m), 509 (m).

$^1$H-NMR [ppm]: (300 MHz, DMSO-d$_6$): δ 1.24-1.87 (br, H1, 3), 2.20 (br, H4), 2.55 (m, H2), 4.15 (br, H12), 6.68 (d, J=7.9 Hz, H15, 17), 7.02 (d, J=7.9 Hz, H14, 18), 12.26 (br, H6).

Determination of the molecular weight has been carried out by size exclusion chromatography (SEC) of the methyl ester.

SEC (THF): M$_W$: 54378 g/mol

M$_N$: 14396 g/mol

D: 3.78

Example 2

Preparation of poly[(N-(4-hydroxy-3,5-(diacrylamidomethyl)benzyl)acrylamide)-co-(acrylic acid)] by Polymer-Analogous Conversion

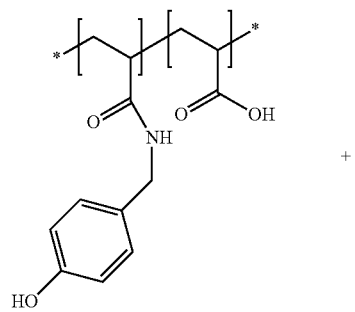

+

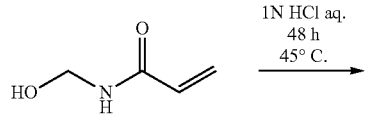

$\xrightarrow{\text{1N HCl aq. 48 h 45° C.}}$

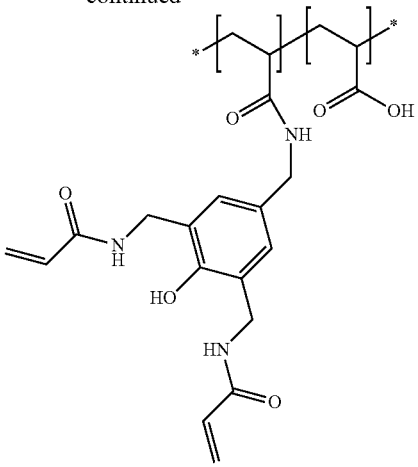

Poly[(N-(4-hydroxybenzyl)acrylamide)-co-(acrylic acid)] (1.5 g), N-(hydroxymethyl)acrylamide (1.6 g, 16 mmol) and 4-tert-butylcatechol (100 mg) were dissolved in 10 mL hydrochloric acid (1 mol/L) and purged with nitrogen for 30 min. The solution was stirred for 48 h at 45° C. Meanwhile, N-(hydroxymethyl)acrylamide (0.5 g in each case) was added after 16, 24 and 40 hours. After complete reaction, dialysis (size exclusion 2000 g/mol) against water was performed for 48 h and the water was removed by freeze-drying.

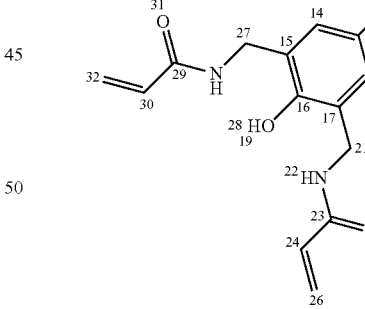

Yield: 0.4 g

IR ν [cm$^{-1}$]: 2936 (m), 2668 (m), 1704 (s), 1650 (m), 1620 (w), 1545 (m), 1449 (m), 1409 (w), 1230 (s), 1165 (s), 1117 (w), 1069 (w), 1018 (w), 976 (w), 803 (s), 622 (m).

$^1$H-NMR [ppm]: (600 MHz, DMSO-d$_6$): δ 1.22-1.83 (br, H1, 3), 2.20 (br, H4), 2.55 (m, H2), 4.15 (br, H12), 4.26 (m, H21, 27), 5.65 (m, H26', 32'), 6.26 (m, H24, 26", 30, 32"), 6.95 (m H14, 18), 12.23 (br, H6).

Example 3

Preparation of poly[(N-(4-hydroxy-3-(acrylamidomethyl)benzyl)acrylamide)-co-(acrylic acid)] by Polymer-Analogous Conversion

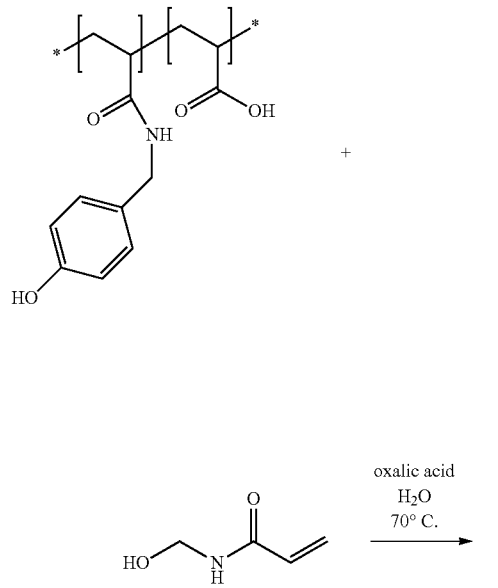

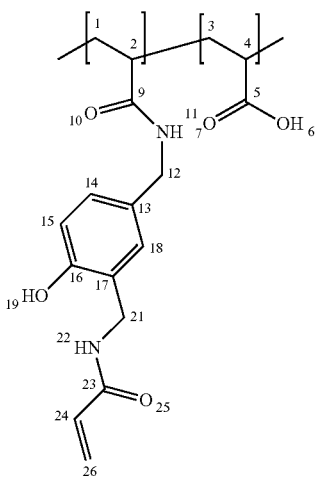

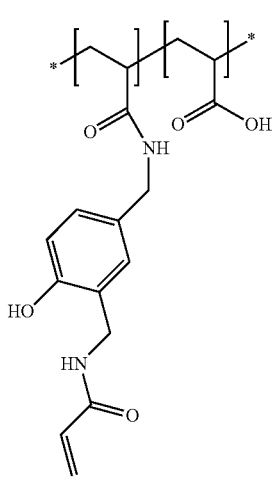

Poly[(N-(4-hydroxybenzyl)acrylamide)-co-(acrylic acid)] (6.5 g), N-(hydroxymethyl)acrylamide (6.5 g, 64 mmol), oxalic acid dihydrate (6 g, 48 mmol) and 3,5-Di-tert-4-butylhydroxytoluene (BHT, 10 mg) were dissolved in 50 mL water and purged with nitrogen for 30 min. The solution was stirred for 24 h at 70° C. After complete reaction, dialysis (size exclusion 2000 g/mol) against water was performed for 48 h and the water was removed by freeze-drying.

Yield: 2.8 g

IR ν [cm$^{-1}$]: 3260 (m), 3067 (m), 2941 (w), 1668 (s), 1631 (s), 1548 (s), 1449 (m), 1408 (s), 1384 (m), 1313 (s), 1296 (w), 1236 (s), 1158 (w), 1115 (w), 1071 (w), 1023 (s), 985 (m), 960 (m), 900 (w), 879 (w), 862 (w), 809 (m), 775 (s), 662 (m), 614 (s), 511 (s).

$^1$H-NMR [ppm]: (300 MHz, DMSO-d$_6$): δ 1.24-1.87 (br, H1, 3), 2.19 (br, H4), 2.55 (m, H2), 4.15 (br, H12), 4.27 (m, H21), 5.63 (m, H26"), 6.26 (m, H24, 26"), 6.74 (m H15, 17), 7.02 (m H14, 18), 12.26 (br, H6).

Application Example 1

An aqueous dental glass ionomer composition was prepared by admixing a liquid and a glass powder.

The liquid was a mixture containing 35 percent by weight of the modified polycarboxylic acid according to Example 3, 15 percent by weight of acrylic acid, 15 percent by weight of a polymerizable, hydrolysis-stable crosslinker according to (E), 1.13 percent by weight of a polymerization photoinitiator system containing camphorquinone as photoinitiator and an amine as polymerization inhibitor, and 33.84 percent by weight of water.

A silanated reactive fluoro aluminosilicate glass with an average particle size of between 0.3 and 2.5 μm was used as glass powder.

The aqueous dental glass ionomer composition was prepared by mixing the liquid 20 to 30 sec. with the glass powder in a ratio of 1 to 2.8, i.e 30 wt % of the liquid and 70 wt % of the glass powder.

Afterwards, six rectangular block specimens with the dimensions 2 mm×2 mm×25 mm were prepared for every composition by introducing the mixed material into metal molds.

These were covered with Melinex foil and pressed between two glass plates. The overall preparation time does not exceed 60 sec. The specimens were cured with a Smart Lite Focus (5×20 sec per side). After light curing, the samples were removed from the mold and the edges deflashed with sand paper. They were stored for 1 h in a 100% humidity environment at 37° C. and afterwards immerged in water at 37° C. for 24 h. The flexural strength of the cured aqueous dental glass ionomer composition was measured using a Zwick testing machine. The arithmetic average and the standard deviation were calculated from six samples of every composition.

The flexural strength obtained for the cured aqueous dental glass ionomer composition was 99.8±18.7 MPa.

Comparative Example 1

As comparative example, a commercial available resin reinforced glass ionomer Fuji II LC was used. The material was dispensed accurately and mixed under room conditions according to the respective manufactures instructions. Afterwards, the specimens were prepared and tested according to the procedure described in Application Example 1.

The flexural strength obtained in comparative example 1 was 64.1±3.3 MPa.

From comparison of the flexural strength obtained in Application Example 1 with that obtained in Comparative Example 1 it can be seen that owing to the polymerizable polyacidic polymer according to the invention, the flexural strength of a cured dental composition can be significantly improved compared to a conventional dental composition.

The invention claimed is:

1. A polymerizable polyacidic polymer having repeating units of the following formula (I):

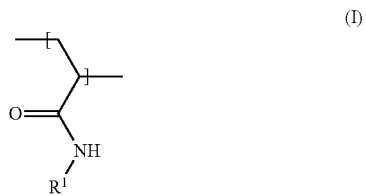

wherein $R^1$ represents a group of the following formula (II):

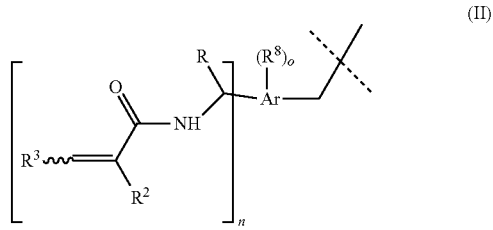

wherein

Ar is an aromatic group which may be further substituted, $R^2$ and $R^3$,
which may be the same or different, independently represent a hydrogen atom, or a $C_{1-6}$ alkyl group which may be substituted with a carboxylic acid group;
R which may be the same or different when more than one R is present, represents a hydrogen atom, a carboxylic acid group, a $COOR^a$ group, a $CONHR^b$ group, or a $CONR^c_2$ group, wherein $R^a$, $R^b$, and $R^c$ represent a $C_{1-6}$ alkyl group;
$R^8$ represents a halogen atom or a group selected from —OH, —$OR^d$, —$NR^eH$, —$NR^eR^f$, —SH, and —$SR^g$, wherein $R^d$, $R^e$, $R^f$, and $R^g$, represent a $C_{1-6}$ alkyl group;
o is an integer of 1 or 2;
n is an integer of 1 to 4;
provided that when o is 2, the $R^8$ cannot be both OH.

2. The polymerizable polyacidic polymer according to claim 1, wherein $R^1$ represents a group of the following formula (II'):

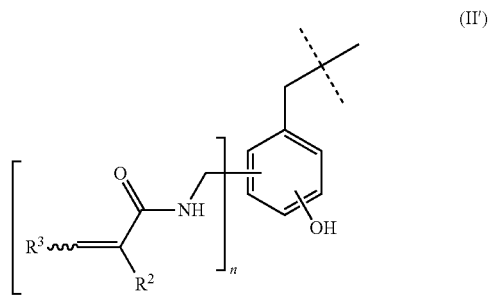

wherein $R^2$, $R^3$ and n are as defined in claim 1.

3. The polymerizable polyacidic polymer according to claim 1, which further comprises acidic repeating units of the following formula (III):

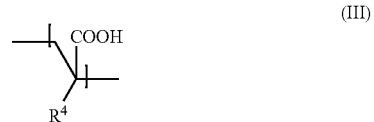

wherein $R^4$ represents a hydrogen atom, or a $C_{1-6}$ alkyl group which may be substituted with a carboxylic acid group.

4. The polymerizable polyacidic polymer according to claim 3, wherein a molar ratio of repeating units of formula (III) and repeating units of formula (I) ([formula (III)]/[formula (I)]) is in a range of 1000:1 to 1:1.

5. The polymerizable polyacidic polymer according to claim 1, which has a molecular weight $M_w$ in a range of 10,000 to 250,000.

6. The polymerizable polyacidic polymer according to claim 1, wherein $R^1$ is a group of the following formula ($II''_a$) or ($II''_b$):

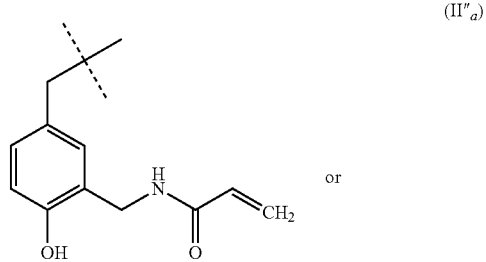

(II″<sub>b</sub>)

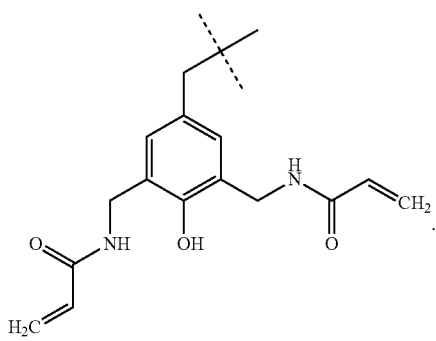

7. A process for preparing a polymerizable polyacidic polymer having repeating units of the following formula (I):

(I)

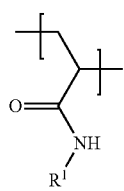

wherein $R^1$ represents a group of the following formula (II):

(II)

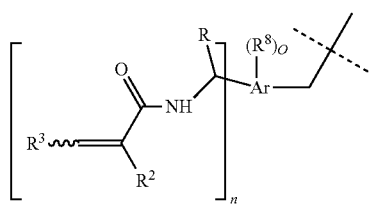

wherein n is an integer of 1 to 4, wherein the process comprises reacting a polyacidic polymer having repeating units of formula (IV):

(IV)

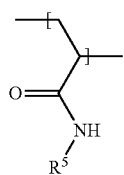

wherein $R^5$ represents a group of formula (V):

(V)

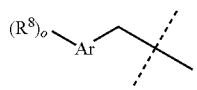

wherein

Ar is an aromatic group which may be further substituted;
$R^8$ represents a halogen atom or a group selected from OH, —$OR^d$, —$NR^eH$, —$NR^eR^f$, —SH, and —$SR^g$, wherein $R^d$, $R^e$, $R^f$, and $R^g$, represent a $C_{1-6}$ alkyl group; and
o is an integer of 1 or 2, provided that when o is 2, the $R^8$ cannot be both OH, with a compound of the following formula (VI)

(VI)

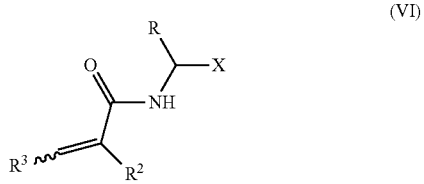

wherein X is a leaving group
$R^2$ and $R^3$,
which may be the same or different, independently represent a hydrogen atom, or a $C_{1-6}$ alkyl group which may be substituted with a carboxylic acid group; and
R which may be the same or different when more than one R is present, represents a hydrogen atom, a carboxylic acid group, a $COOR^a$ group, a $CONHR^b$ group, or a $CONR^c_2$ group, wherein $R^a$, $R^b$, and $R^c$ represent a $C_{1-6}$ alkyl group.

8. The process according to claim 7, wherein
(a) X is a hydroxyl group, and/or
(b) the reaction is carried out in the presence of an organic acid.

9. An aqueous dental composition comprising a polymerizable polyacidic polymer, wherein the polymerizable polyacidic polymer has repeating units of the following formula (I):

(I)

wherein $R^1$ represents a group of the following formula (II):

(II)

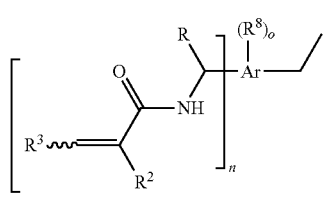

wherein

Ar is an aromatic group which may be further substituted,
$R^2$ and $R^3$,
which may be the same or different, independently represent a hydrogen atom, or a $C_{1-6}$ alkyl group which may be substituted with a carboxylic acid group;

R which may be the same or different when more than one R is present, represents a hydrogen atom, a carboxylic acid group, a $COOR^a$ group, a $CONHR^b$ group, or a $CONR^c{}_2$ group, wherein $R^a$, $R^b$, and $R^c$ represent a $C_{1-6}$ alkyl group;

$R^8$ represents a halogen atom or a group selected from —OH, —$OR^d$, —$NR^eR^f$, —SH, and —$SR^g$, wherein $R^d$, $R^e$, $R^f$ and $R^g$, represent a $C_{1-6}$ alkyl group;

o is an integer of 1 or 2;

n is an integer of 1 to 4;

provided that when o is 2, the $R^8$ cannot be both OH.

10. The aqueous dental composition according to claim 9, which further comprises a particulate glass filler.

11. The aqueous dental composition according to claim 9, comprising a polymerizable monomer, a polymerisation initiator and optionally a stabilizer.

\* \* \* \* \*